US008357189B2

(12) United States Patent
Ugajin et al.

(10) Patent No.: US 8,357,189 B2
(45) Date of Patent: Jan. 22, 2013

(54) PHYSIOLOGY ENHANCING DEVICE

(75) Inventors: Toru Ugajin, Tochigi (JP); Michihito Igaki, Tokyo (JP); Kazutaka Yamashita, Tochigi (JP); Katsutoshi Hara, Tokyo (JP); Yoshinao Nagashima, Tokyo (JP); Shuji Ishikawa, Tokyo (JP); Ichiro Sakamoto, Tokyo (JP)

(73) Assignee: Kao Corporation, Tokyo (JP)

( * ) Notice: Subject to any disclaimer, the term of this patent is extended or adjusted under 35 U.S.C. 154(b) by 1322 days.

(21) Appl. No.: 11/817,524

(22) PCT Filed: Mar. 3, 2006

(86) PCT No.: PCT/JP2006/304138
§ 371 (c)(1),
(2), (4) Date: Mar. 5, 2008

(87) PCT Pub. No.: WO2006/093285
PCT Pub. Date: Sep. 8, 2006

(65) Prior Publication Data
US 2009/0062890 A1 Mar. 5, 2009

(30) Foreign Application Priority Data

Mar. 4, 2005 (JP) ................................. 2005-061108
Mar. 4, 2005 (JP) ................................. 2005-061612
Aug. 30, 2005 (JP) ................................. 2005-250295

(51) Int. Cl.
*A61F 7/00* (2006.01)

(52) U.S. Cl. ...................................................... 607/108

(58) Field of Classification Search .................. 607/108, 607/109–112, 96; 604/304–308; 602/41–59, 602/2
See application file for complete search history.

(56) References Cited

U.S. PATENT DOCUMENTS
(Continued)

FOREIGN PATENT DOCUMENTS
EP  0 526 637 A1  2/1993
EP  1 147 752 A1  10/2001
(Continued)

OTHER PUBLICATIONS

JP 2001-187727 (Kao Corp.), Jul. 10, 2001.*

(Continued)

*Primary Examiner* — Manuel Mendez
(74) *Attorney, Agent, or Firm* — Oblon, Spivak, McClelland, Maier & Neustadt, L.L.P.

(57) ABSTRACT

A physiology enhancing device for improving physiological functions of a human body, etc., which comprises a heat generating element making use of chemical energy and a sheet interposed between the heat generating element and a body surface of a wearer, and which is designed to supply steam generated from the heat generating element while the device is applied to the body surface. The device exhibits steam generating capability for 2 hours or longer and, while applied to the body surface, raises the body surface temperature to a temperature from 38° C. to lower than 42° C. within one hour from the application. The sheet interposed between the heat generating element and the body surface preferably has a function of regulating air feed to the heat generating element and a function of transferring the heat of the physiology enhancing device to the body surface and preferably has a total thickness of 0.05 to 1.5 mm.

24 Claims, 17 Drawing Sheets

U.S. PATENT DOCUMENTS

| | | |
|---|---|---|
| 6,409,746 B1 | 6/2002 | Igaki et al. |
| 2002/0045923 A1 | 4/2002 | Tone et al. |
| 2006/0151136 A1 | 7/2006 | Kumamoto et al. |
| 2010/0139639 A1 | 6/2010 | Igaki et al. |

FOREIGN PATENT DOCUMENTS

| | | |
|---|---|---|
| EP | 1 181 911 A1 | 2/2002 |
| JP | 1 250252 | 10/1989 |
| JP | 2-182253 A | 7/1990 |
| JP | 3 173815 | 7/1991 |
| JP | 5 170644 | 7/1993 |
| JP | 7 197087 | 8/1995 |
| JP | 8-80317 | 3/1996 |
| JP | 9 196864 | 7/1997 |
| JP | 10 137193 | 5/1998 |
| JP | 2000-5210 | 1/2000 |
| JP | 2000-166955 | 6/2000 |
| JP | 2000-232989 | 8/2000 |
| JP | 2001-031559 A | 2/2001 |
| JP | 2001 87302 | 4/2001 |
| JP | 2001 95832 | 4/2001 |
| JP | 2001 187727 | 7/2001 |
| JP | 2001-245915 | 9/2001 |
| JP | 2002 58699 | 2/2002 |
| JP | 2002-65714 | 3/2002 |
| JP | 2002-78727 | 3/2002 |
| JP | 2002-143203 | 5/2002 |
| JP | 2002-200108 | 7/2002 |
| JP | 2004-8564 | 1/2004 |
| JP | 2004-202198 A | 7/2004 |
| JP | 2005 21673 | 1/2005 |
| JP | 2005 199051 | 7/2005 |
| WO | WO 2005/058213 | 6/2005 |

OTHER PUBLICATIONS

JP 2005-21673 (Kao Corp.), Jan. 27, 2005.*
JP 2005-199051 (Kao Corp.), Jul. 28, 2005.*
JP 2002-58699 (Kao Corp.), Feb. 26, 2002.*
Japanese Notice of Rejection issued Jan. 25, 2011, in Patent Application No. 2006-058568 (with English-language translation).
Japanese Office Action issued Mar. 1, 2011, in Patent Application No. 2006-165025 (with English-language translation).
Office Action issued Mar. 22, 2011 in Japan Application No. 2006-058564 (With English Translation).
European Office Action issued Jun. 17, 2011, in Patent Application No. 06 728 617.9.
Extended Supplementary European Search Report issued Jul. 12, 2010 in European Application No. 06 72 8617.
Japanese Office Action issued Jul. 13, 2010 in Japanese Application No. 2005-323801(with English translation).
European Office Action Issued Aug. 3, 2012 in Patent Application No. 06 728 617.9.
Communication pursuant to Article 94(3) EPC issued Mar. 13, 2012, in Europe Application No. 06 728 617.9.

* cited by examiner

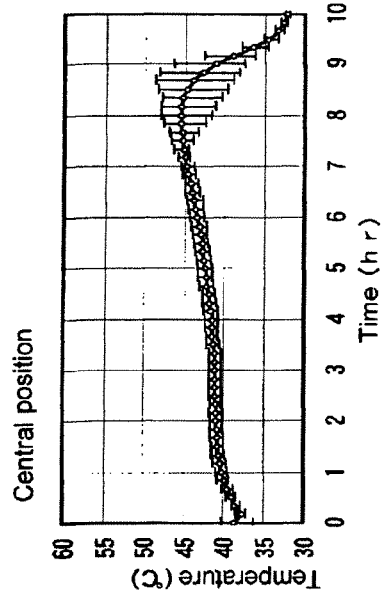
Fig.15(b) Central position
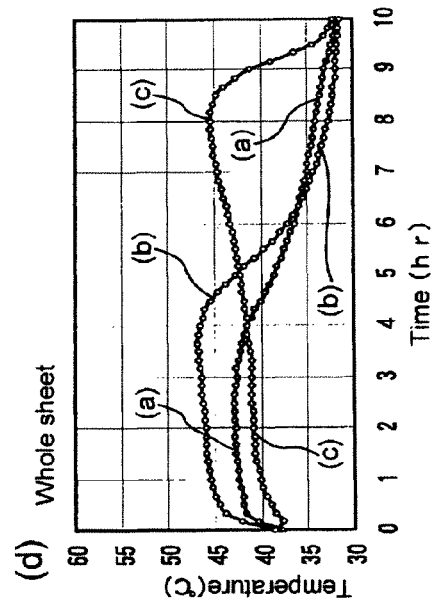
Fig.15(d) Whole sheet
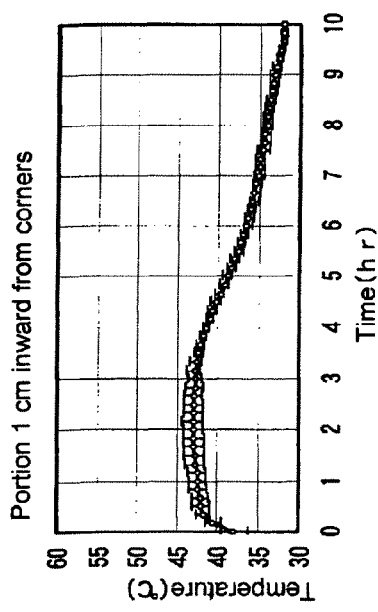
Fig.15(a) Portion 1 cm inward from corners
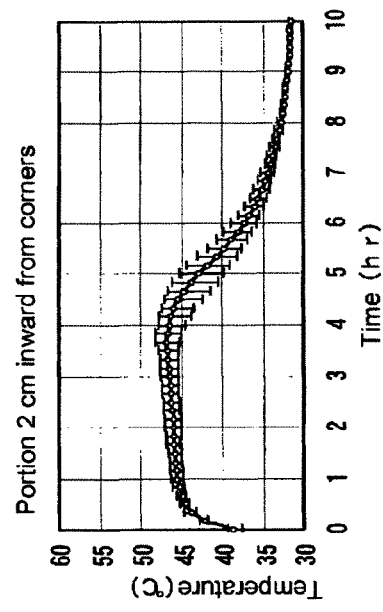
Fig.15(c) Portion 2 cm inward from corners

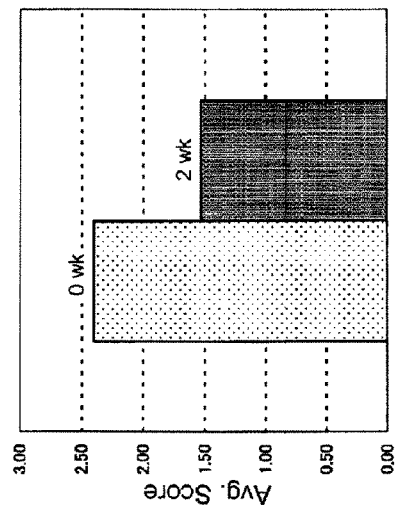
Fig.22(a) Overall Evaluation
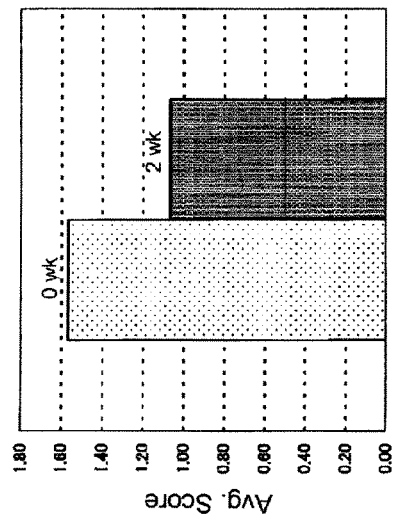
Fig.22(b) Heavy Feeling
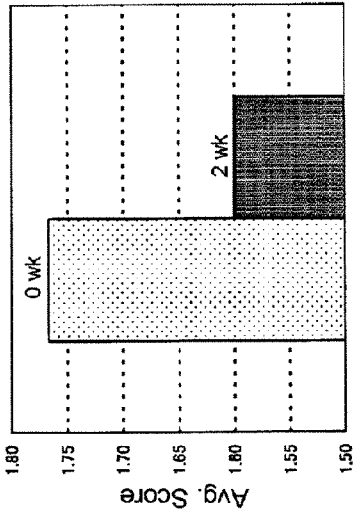
Fig.22(c) Pain
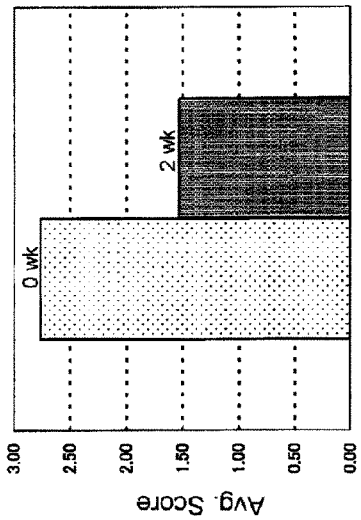
Fig.22(d) Listless Feeling

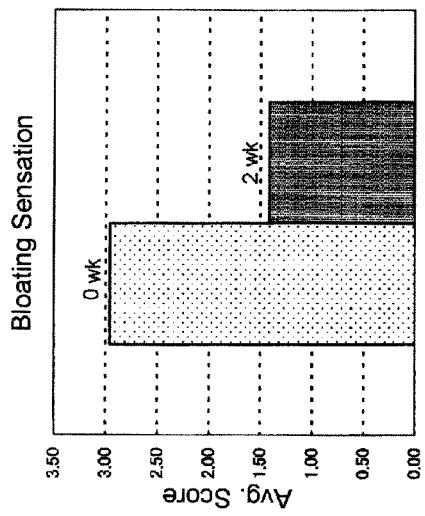
Fig.23(a) Constipation
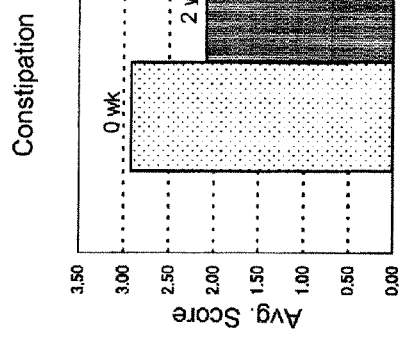
Fig.23(b) Bloating Sensation
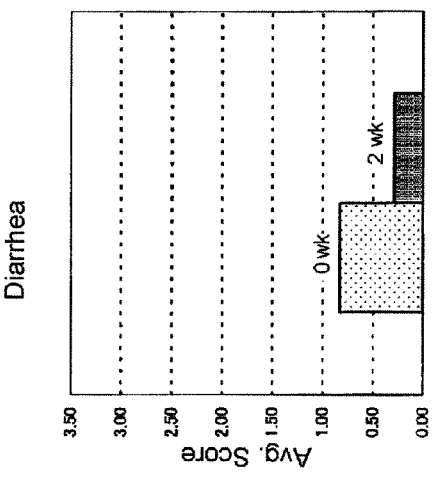
Fig.23(c) Diarrhea
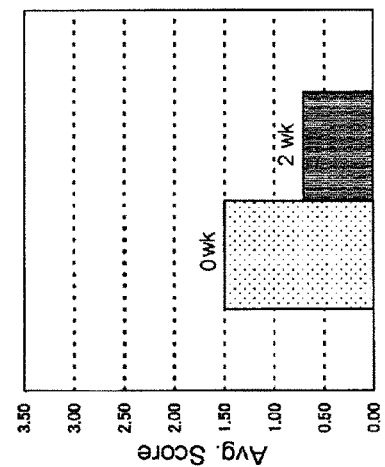
Fig.23(d) Abdominal Pain

PHYSIOLOGY ENHANCING DEVICE

TECHNICAL FIELD

The present invention relates to a physiology enhancing device using steam. It also relates to a moist heating device.

BACKGROUND ART

With the changes in lifestyles, the health-consciousness of overall society shows an inclination toward self-medication. With this trend, awareness of daily health care is increasing. Typical health problems commonly experienced by adults are lower back pain, shoulder pain, oversensitivity to cold, blurred vision, menstrual cramps, joint pains, and the like. The recent advances of IT in offices have also given rise to additional health problems, such as pains of the lower back, shoulders or neck and eyestrain. It is is predicated that to alleviate, cure or prevent these symptoms through daily life at home will be a popular choice. For instance, thermotherapy with a disposable heat pack body warmer (a heat generating element containing an oxidizable metal) applied to an affected part (e.g., the lower back) is known to help provide pain relief. It is expected that such thermotherapy will become increasingly popular on the individual level.

Commonly assigned JP 2002-65714A and JP 2002-78727A propose an eye mask type vision improving device and an eye mask type meibomian gland function improving device both of which supply steam to and around the eyes. These treating devices supply steam at a temperature that does not become a noxious stimulus to and around the eyes thereby to relax and improve the ciliary muscle, improve the vision, or improve the meibomian gland function. Seeing that the devices are designed to be applied to and around the eyes, the time of supplying steam is so short as not to cause a noxious stimulus, i.e., several tens of minutes at the most. These devices aim at improvement of vision or the meibomian gland function. However, the publications cited above do not mention whether the devices are capable of improving other physiological functions. Neither do they mention whether the devices give a wearer a feeling of relaxation.

Apart from the treating devices, commonly assigned EP 1147752A1 proposes a steam generating unit that supplies steam to a wearer's skin or mucous membrane. In a mode of application, the steam generating unit is designed to leave a gap of 5 mm or more between the unit and the bodily part, e.g., the skin or mucous membrane. However, because this mode of application requires a large quantity of steam, it is not easy to secure prolonged moist heat generation.

DISCLOSURE OF THE INVENTION

The present invention provides a device for enhancing the physiology of a human body, etc. (hereinafter "physiology enhancing device"). The physiology enhancing device includes a heat generating element that makes use of chemical energy and a sheet interposed between the heat generating element and a body surface of a wearer. The physiology enhancing device is designed to supply steam generated from the heat generating element while the device is applied to the body surface. And the physiology enhancing device has steam generating capability for 2 hours or longer. When applied to the body surface, the physiology enhancing device raises the body surface temperature to a temperature from 38° C. to lower than 42° C. within one hour.

The present invention provides a device for enhancing the physiology of a human body, etc. (hereinafter "physiology enhancing device"). The physiology enhancing device includes a heat generating element that makes use of chemical energy and a sheet interposed between the heat generating element and a body surface of a wearer. The physiology enhancing device is designed to supply steam generated from the heat generating element while the device is applied to the body surface. And the physiology enhancing device has steam supplying capability in a measuring environment of 20° C. and 40% RH such that the water content of the horny layer of the skin site to which the device is applied reaches 0.25 g/cm$^3$ or more after 0.5 hours from the start of application and that the water content of that level is maintained for 5 hours or longer from the start of application.

The present invention also provides a moist heating device. The moist heating device includes a heat generating element that makes use of chemical energy and is configured to supply steam while applied to a body surface of a wearer with a sheet interposed between the heat generating element and the body surface. While applied to the wearer's body surface, it supplies steam from the heat generating element. The sheet includes at least an air permeable portion having a water vapor transmission rate of 150 to 2000 g/(m$^2$·24 hr) (JIS Z0208, 40° C., 90% RH). The heat generating element has steam generating capability such that the amount of steam released per unit time reaches the maximum in 0.5 to 25 minutes from the start of heat generation. The sheet interposed between the heat generating element and the body surface has a function of regulating air feed to the heat generating element and a function of transferring the heat of the moist heating device to the body surface and has a total thickness of 0.05 to 1.5 mm.

BRIEF DESCRIPTION OF THE DRAWINGS

FIGS. 15(a), 15(b), 15(c), and 15(d) are graphs showing the results of measuring heat generation temperatures of a physiology enhancing device according to the present invention.

FIG. 22(a), FIG. 22(b), FIG. 22(c), and FIG. 22(d) are each a graph showing the lower back pain reducing effect by a moist heating device according to the present invention.

FIG. 23(a), FIG. 23(b), FIG. 23(c), and FIG. 23(d) are each a graph showing the abdominal symptom reducing effect by a moist heating device according to the present invention.

BEST MODE FOR CARRYING OUT THE INVENTION

Figure 1A:
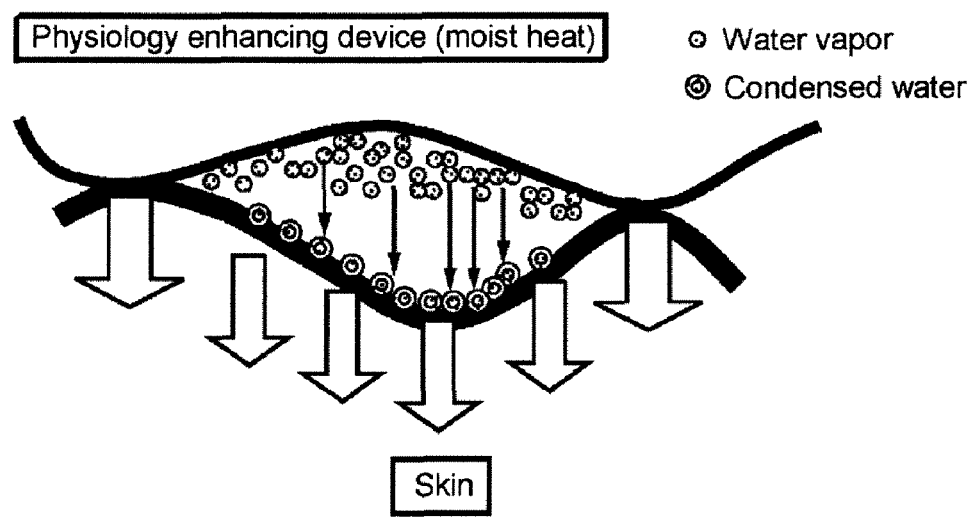
FIG. 1(a) is a model of moist heat conduction.

The present invention relates to a physiology enhancing device capable of improving various physiological functions of human bodies, etc. The present invention also relates to a moist heating device capable of making a wearer feel relaxed.

A first aspect of the present invention will be described. The physiology enhancing device of the invention is primarily applicable to a human body surface. The bodily parts to which the device is applicable include, but are not limited to, the lower back, the abdomen, the neck, shoulders, and various joints and so on as desired. The physiology enhancing device is used as applied to a body surface. As used herein, the expression "applied to a body surface" means that the physiology enhancing device is brought into contact with a body surface via a sheet that allows steam to pass therethrough and serves as a spacer or a fixing means.

The physiology enhancing device of the invention is characterized by (1) having a heat generating element that generates heat making use of chemical energy and (2) supplying steam generated from the heat generating element to a body surface. Therefore, the heat generating element can be said to be a steam generating element. The physiology enhancing device is particularly characterized by continuously generating steam for a prolonged period of time. In what follows, heat applied to a body surface while being accompanied by steam is called "moist heat", whilst heat applied to a body surface without being accompanied by steam, for example, the heat generated from commercially available disposable heat pack body warmers is called "dry heat".

The chemical energy that can be made use of in the present invention includes heat of oxidation generated by oxidation reaction of an oxidizable metal, heat of neutralization generated by neutralization reaction between an acid and an alkali, and heat of hydration of an inorganic salt (e.g., calcium chloride, magnesium chloride, calcium oxide, magnesium oxide or zeolite). It is preferred to use, among them, heat of oxidation generated by oxidation reaction of an oxidizable metal in view of ease of handling, relatively high heat value, and possibility of providing an easy-to-carry, compact product.

The composition of the heat generating element is decided as appropriate according to the type of the chemical energy to be utilized. For example, in using heat of oxidation generated by oxidation reaction of an oxidizable metal, the heat generating element is made of a steam generative composition containing a powdered metal (e.g., iron, aluminum, zinc or copper), a salt as a catalyst (e.g., an alkali metal chloride such as sodium chloride or potassium chloride or an alkaline earth metal chloride such as calcium chloride or magnesium chloride), and water. The steam generative composition can further contain a water retaining agent (e.g., vermiculite, calcium silicate, silica gel, porous silicic substances, alumina, pulp, wood meal or absorbent polymers), a reaction accelerator (e.g., activated carbon, carbon black or graphite), and the like.

In using heat of neutralization between an acid and an alkali or heat of hydration of an inorganic salt, the heat generating element can be composed of a heating part where heat of neutralization or hydration is generated and an evaporation part where water vapor is released by the heat generated in the heating part. In the heating part the reactants are separated by a partition. The partition is broken whenever steam generation is demanded to cause the reaction to proceed. The evaporation part is made of, for example, a fiber aggregate (such as paper, woven fabric or nonwoven fabric) or a porous material each impregnated with water or a water-containing polymer gel drawn into sheeting and is configured to release steam by the heat generated in the heating part.

The physiology enhancing device according to the first aspect of the invention includes a heat generating element that makes use of chemical energy. The device supplies steam generated from the heat generating element while applied to a body surface of a wearer with a sheet interposed between the heat generating element and the body surface. The device exerts steam generating capability for at least 2 hours. The physiology enhancing device has steam generating capability such that, when applied to a body surface, it raises the body surface temperature to a temperature of 38° C. or higher and lower than 42° C. within one hour. Applying the physiology enhancing device having such steam generating capability to a body surface via a sheet brings about significant improvement on various physiological functions of a human body as will be verified in Examples given later.

FIG. 1(a) schematically illustrates the physiology enhancing device applied to a body surface. Steam generated from the physiology enhancing device moves through a space between the device and the skin (mass movement) and reaches the skin to conduct heat (contact heat transfer). On reaching the skin, the steam condenses into water, and the heat generated (heat of condensation) is transmitted to the skin. Thus, the physiology enhancing device utilizing moist heat achieves high heat transfer efficiency in transferring heat to the skin.

Figure 1B:
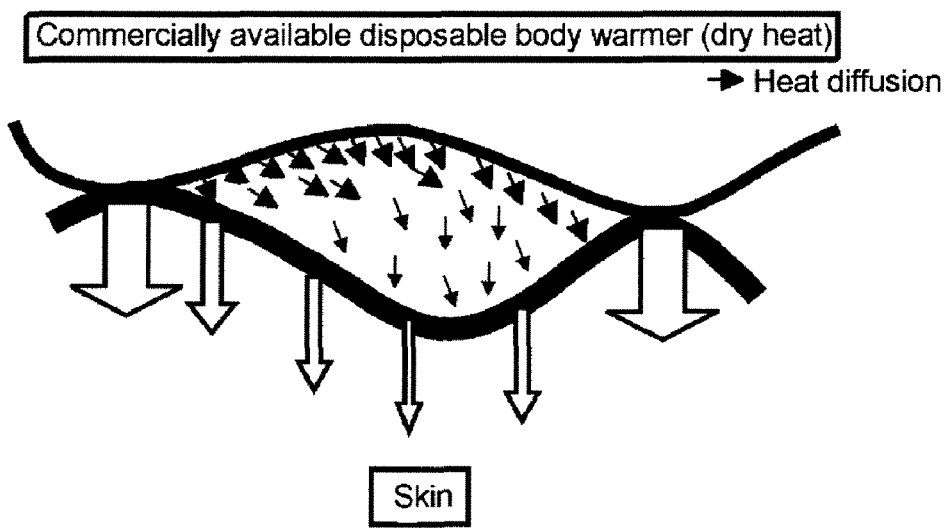
FIG. 1(b) is a model of dry heat conduction.

FIG. 1(b) schematically illustrates how dry heat is conducted in comparison with FIG. 1(a). Dry heat, namely the heat of a commercially available disposable heat pack body warmer is transferred through heat diffusion in air molecules.

Accordingly, dry heat achieves a low heat transfer efficiency, failing to transmit sufficient heat to the skin.

Figure 2A:
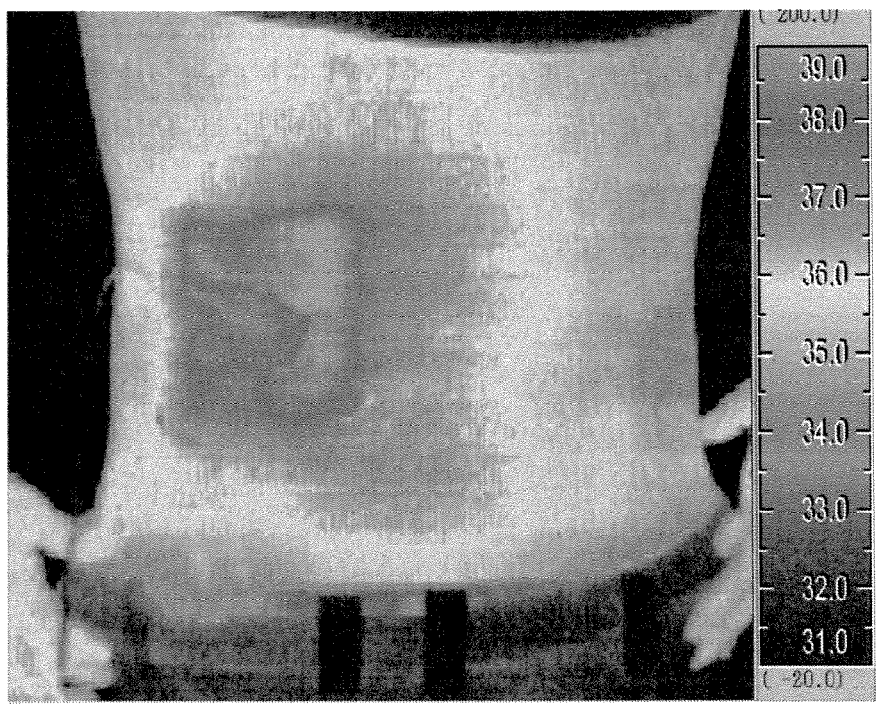
FIG. 2(a) is a thermogram of a physiology enhancing device according to the present invention applied to the lower back of a wearer.
Figure 2B:
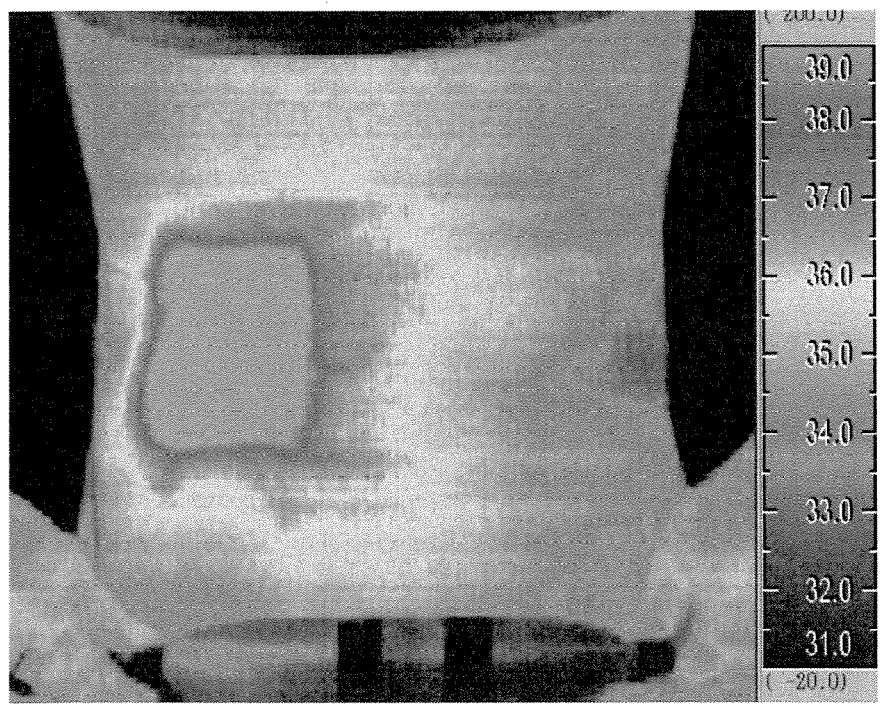
FIG. 2(b) is a thermogram of a dry heat type body warmer applied to the lower back of a wearer.

Thus, warming a human body with moist heat is more effective than with dry heat, with the heating temperature itself being equal, which is apparent from the results of thermography shown in FIGS. 2(a) and 2(b). FIG. 2(a) represents a thermogram of a moist heat type physiology enhancing device of the invention applied to the lower back of a human body, and FIG. 2(b) a thermogram of a dry heat type body warmer applied to the lower back of a human body (see the method of measurements of FIGS. 13(a) to (c) described later). The body surface temperature at the surroundings of the application site rises higher in FIG. 2(a) (the present invention) than in FIG. 2(b) in which the dry heat type body warmer is applied. This provides confirmation that the moist heat type physiology enhancing device accomplishes remarkable heat transfer to the surroundings of the application site. The reason why is considered to be that the heat conductivity (the definition of which will be given later) from the heat generating element to the skin increases by the action of steam generated from the heat generating element. It is also considered that the steam having reached the skin releases the heat of condensation, which is then transferred to the skin. In contrast, dry heat conductivity is lower because it is transferred only through heat diffusion. The higher heat transfer efficiency of moist heat than of dry heat seems to be attributed to these reasons.

It has been confirmed that warming various parts of a human body, such as the lower back or a shoulder, with moist heat having the above-described characteristics results in greater promotion of systemic blood circulation and a greater rise in the peripheral body temperature than with dry heat. It has also been testified that the increase in the peripheral temperature outlasts the heat application for several tens of minutes. As stated previously, this is because moist heat is transmitted at a higher rate so that it is more capable of increasing the deep body temperature than dry heat. It is considered that a rise in temperature deep in the body stimulates the heat center via the autonomic nerves, whereby blood vessels dilate to increase the flow and raises the peripheral temperature. Thus, the physiology enhancing device of the invention brings about not only a rise in the temperature and improvement of blood circulation of the body part where it is applied but also improvement of systemic blood circulation, an increase in the peripheral temperatures such as the finger tip temperatures, and reduction of oversensitivity to cold. Furthermore, since moist heat effectively transfers heat, it delivers much heat deep under the skin even when the temperature of the heat generating element is low. Therefore, the physiology enhancing device of the invention is effective in reducing the risk of a low temperature burn that has been a problem with commercially available heat pack body warmers.

The body surface temperature and the deep body temperature were measured as follows. All the measurements were taken in an environment of 20° C. and 40% RH. A physiology enhancing device held in the holder illustrated in FIGS. 7(a) and 7(b) (described infra) was attached to the lower back of healthy subjects whose armpit temperatures ranged between 35° C. and 37° C. and whose lower back surface temperatures ranged between 31° C. and 35° C. The constrictive force of the holder was 4 to 6N. A measuring instrument was attached to each subject, and the subject was asked to rest for 30 minutes. The subjects worn clothing having a clo value of 0.3 to 1.5 so that the environmental measuring conditions might be kept constant. A clo value is a measure of thermal insulation of clothing. ASHRAE (American Society of Heating, Refrigerating and Air-Conditioning Engineers) defines that one clo is an insulation value required to keep a seated normal male subject comfortable (with a mean skin temperature of 33° C.) at an air temperature of 21.2° C. and 50% RH in an air movement of 10 cm/s. One clo is equivalent to 0.18° $Cm^2$ h/kcal (=0.155° $Cm^2/W$).

The body surface temperature was measured at a position right under the heat generating element of the physiology enhancing device attached to the subject's body (lower back) and at a position 2 cm outward from the edge of the heat generating element. The deep body temperature was measured at a position 2 cm outward from the edge of the heat element and 10 mm below the skin. Both the body surface temperature (right under the heat generating element) and the deep body temperature were measured with a body thermometer Coretemp CM-210 equipped with a skin temperature probe PDK161 and a deep body temperature probe PD1, all from Terumo Corp. The body surface temperature at a position 2 cm outward from the heat generating element was measured with a thermistor-thermometer LTST08-12 from Gram Corp.

The sheet that is to be interposed between the heat generating element and the body surface when the physiology enhancing device of the invention is applied to the body has its characteristics designed so that the body surface temperature of the application site may rise to a temperature of from 38° C. to lower than 42° C. within one hour from the application, taking into consideration the physiology enhancing effects, safety to human body, and comfort to wear. Specifically, the characteristics of the sheet are designed so that the sheet may perform both a function of regulating air feed to the heat generating element and a function of transferring the heat of the heat generating element to the body surface. The expression "rise to a temperature of from 38° C. to lower than 42° C. within one hour" as used herein is intended to include a case in which the body surface temperature once rises to or above 42° C. due to overshoot but is stabilized in a range of from 38° C. to lower than 42° C. within one hour.

The fact that the physiology enhancing device of the invention achieves an increased heat transfer efficiency can be supported by measuring heat conductivity. However, it is difficult to measure the heat conductivity of the physiology enhancing device while in actual use on a human body. In the present invention, therefore, the inventors developed a model measurement system, with which to measure the heat conductivity.

Figure 3:
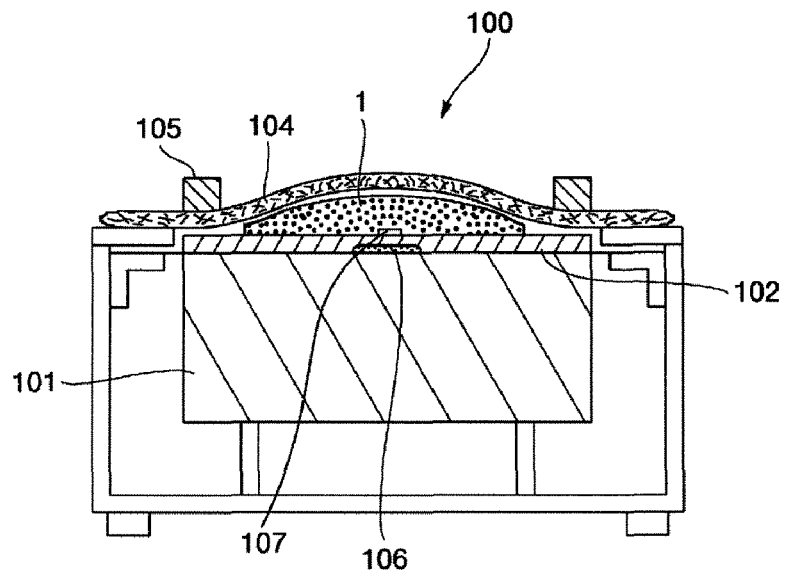
FIG. 3 schematically illustrates a model measurement system for measuring heat conductivity.

FIG. 3 illustrates the method of heat conductivity measurement using a model measurement system made by reference to JIS S4100. The measuring environment is 20° C. and 50% RH. The model measurement system 100 includes a hot bath 101, a polypropylene plate 102 (thickness: 7 mm) put on the hot bath 101, and eight thicknesses of 100% cotton flannel 104 (5.905 tex×2 doubled yarn) covering the plate 102. The hot bath 101 corresponds to a human body. The surface temperature of the hot bath 101 corresponding to the body surface temperature is set at a general body temperature, 36.0° C. A physiology enhancing device 1 is disposed between the plate 102 and the flannel 104, and the temperature and heat conductivity are measured. As used herein, the term "heat conductivity" refers to the heat conductivity from the heat generating element of the physiology enhancing device 1 to the surface of the hot bath 101 defined to be a body surface. A frame 105 is placed on the flannel 104 to surround and fix the physiology enhancing device 1 taking care not to leave a gap between the flannel 104 and the plate 102. A heat flux meter 106, a sensor for measuring a heat flux, is put between the hot bath 101 and the plate 102 right beneath the physiology enhancing device 1. In addition to the heat flux meter 106, a thermocouple 107 is put between the physiology enhancing device 1 and the plate 102. The thermocouple 107 is for measuring the heat generation temperature of the physiology enhancing device 1. PHF01 (trade name) supplied from Prede Co., Ltd., Tokyo, Japan was used as the heat flux meter 106.

In the measurement with the model measurement system 100 illustrated in FIG. 3, signals (voltages) sent from the heat flux meter 106 and the thermocouple 107 were processed on a personal computer to measure and record the heat flux and the heat generation temperature of the physiology enhancing device 1. These results were further processed through a personal computer program to give the heat conductivity. Data processing on a personal computer was done using commercially available software.

The physiology enhancing device 1 is used as applied to a human body with its portion from which steam generated in the heat generating element is releasable (hereinafter "steam release portion") facing to the body. Accordingly, in the model measurement system, too, the heat conductivity measurement should be done by placing the physiology enhancing device 1 with its steam release portion facing the hot bath 101.

Comparison was made between the heat conductivities of moist heat and dry heat to the hot bath 101 in the model measurement system. The physiology enhancing device 1 was applied to the plate 102 of the model measurement system, and the heat conductivity from the heat generating element of the device 1 to the hot bath 101 was obtained. While the temperatures of the moist heat and the dry heat reached after a one hour application period were equal (42.0° C.), the heat conductivities were as follows.

Moist heat: 0.046 W/(m·° C.)
Dry heat: 0.039 W/(m·° C.)

The heat conductivities measured after a 2-hour application were:

Moist heat: 0.048 W/(m·° C.)
Dry heat: 0.032 W/(m·° C.)

These results verify that moist heat conductivity is significantly higher than dry heat conductivity. The measurement results obtained from the model system lead to the consideration that heat transfer from the physiology enhancing device 1 to a human body is further enhanced by the steam to bring about further pronounced improvements of physiological functions.

It is preferred, as is understandable from the above results, that the physiology enhancing device 1 of the invention has such steam generating capability as to achieve a heat conductivity of 0.04 to 0.06 W/(m·° C.), more preferably 0.045 to 0.055 W/(m·° C.), in transferring the heat of its heat generating element to the hot bath 101 when brought into contact with the plate 102 of the model measurement system in an environment of 20° C. and 50% RH.

The dry heat conductivity, i.e., the heat conductivity of air is 0.096 kJ/(m·hr·° C.) (=0.027 W/(m·° C.)) (40° C.) while that of water is higher than that, i.e., 2.40 kJ/(m·hr·° C.) (=0.67 W/(m·° C.) (60° C.). It is believed from these values, taken in conjunction with the above-described results, that steam increases heat conductivity, that is, transfer of heat is enhanced by steam. Thus, the physiology enhancing device of the present invention, which makes use of moist heat, extremely increases heat conductivity from the device to a human body.

In view of effective improvement on physiological functions, it is preferred for the physiology enhancing device of the invention to have a long duration of steam generation. Specifically, the physiology enhancing device has steam generating capability for 2 hours or longer, preferably 2 to 12 hours, more preferably 3 to 6 hours, in order to enhance physiological functions by shifting the autonomic nervous system balance to the parasympathetic dominance. Additionally, it is preferred for the physiology enhancing device of the invention to have heat generating capability and steam generating capability such that, while applied to a body surface, the device maintains the body temperature at a temperature from 38° C. to lower than 42° C., more preferably from 38° C. to lower than 41° C., for a period of 2 to 12 hours, more preferably 3 to 6 hours.

A second aspect of the present invention is then described. Unless otherwise specified, the description of the first aspect applies appropriately to the second one. The physiology enhancing device according to the second aspect is characterized by its ability to increase the water content of the horny layer of the skin of the application site over an ordinary level. The physiology enhancing device of the second aspect has steam supplying capability such that the water content of the horny layer of the skin of the application site reaches 0.25 g/cm$^3$ or more after 0.5 hours from the start of application and that the water content of that level is maintained for 5 hours or longer from the start of application under a measuring environment of 20° C. and 40% RH. In what follows, the term "water content of the horny layer" refers to a value as measured in a measuring environment of 20° C. and 40% RH. Applying the physiology enhancing device having such steam generating capability to the surface of a human body markedly improves various physical functions.

The water content of the horny layer is influential on the heat conductivity of the horny layer. It is known that the horny layer forming the outermost layer of the skin has a lower heat conductivity because of its smaller water content than the epidermis or dermis beneath the horny layer. Moist heat supplied by the physiology enhancing device of the invention moistens the horny layer having such a condition to increase the water content of the horny layer. As a result, the heat conductivity of the horny layer increases. According to the present invention, the increase in the skin's heat conductivity and the aforementioned contact heat transfer by the steam of moist heat (see FIG. 1(*a*)) synergistically secure deep and diffusive skin penetration of heat.

The water content of the horny layer is measured by TDR (time domain reflectometry). In TDR, the tip of a probe is brought into contact with the skin to apply microwaves of 10 GHz to the skin, and the reflected waves are detected with the probe. Because the reflected waves vary depending on the dielectric characteristics, i.e., orientation of water molecules, of the skin, the water content of the skin can be determined by detecting the reflected waves. In TDR, The depth of measurement differs according to the diameter of the probe. A larger diameter probe is capable of measuring the water content in a deeper tissue. In the present invention the water contents from the skin surface to a depth of 20 μm were measured using a TDR probe A (from Toko Denshi Co., Ltd.; outer diameter: 0.7 mm). A Digitizing oscilloscope 54750A (trade name) from Hewlett Packard was used, to which the probe was connected.

As previously stated, the physiology enhancing device of the invention has steam supplying capability such that the water content of the horny layer of the skin to which the device is applied reaches 0.25 g/cm$^3$ or more after 0.5 hours from the start of application and that the water content of that level is maintained for 5 hours or longer from the start of application. The steam supplying capability of the physiology enhancing device is preferably such that the water content of the horny layer of the skin of the application site reaches 0.25 to 0.39 g/cm³ after 0.5 hours from the start of application and that the water content of that level is maintained for 5 hours or longer from the start of application. There is no particular upper limit to the water content of the horny layer, and a higher water content is preferred. Theoretically, nevertheless, the upper limit would be about 0.70 g/cm³, the water content of subcutaneous tissues of human body. The phrase "the start of application" as used herein refers to the time point when the physiology enhancing device is applied to the skin immediately after being brought into a state ready to generate heat. Hence, when the physiology enhancing device is applied to the skin to take the water content measurement after an elapse of a certain time from the onset of heat generation, the time point of application is not regarded as "the start of application" of the physiology enhancing device.

In order to increase the horny layer's water content, it is advantageous that the space formed between the physiology enhancing device applied to the skin and the skin of the application site is sufficiently moistened. From this viewpoint, it is preferred for the physiology enhancing device of the invention to have such steam generating capability that the humidity between the device and the skin of the application site becomes 50% RH or higher after 0.5 hours from the start of application and that the humidity of that level is maintained for 5 hours or longer from the start of application in a measuring environment of 20° C. The above-defined humidity is more preferably 60% RH or higher, even more preferably 70% RH or higher. The higher the humidity, the more it is preferred (accordingly, the upper limit of the humidity is ideally 100%). In what follows, the term "humidity between the physiology enhancing device and the skin" as used herein means a value measured in a room of 20° C. and 40% RH.

A third aspect of the present invention is now described. Unless otherwise specified, the description of the first and second aspects applies appropriately to the third one. The third aspect relates to a moist heating device having a heat generating element that applies steam to the wearer's body surface to make the autonomic parasympathetic nervous system dominant. The moist heating device is characterized especially by having a longer duration of steam generation than the treating devices that apply steam to the wearer's eyes as stated in Background Art.

The vision improving device and the meibomian gland function improving device disclosed in JP 2002-65714A and JP 2002-78727A (see Background Art) have the heat generation temperatures controlled by the amount of air flow or water vapor transmission rate of an air permeable sheet. However, the study by the inventors of the present invention revealed that how the temperature starts to rise is governed by the heat generation characteristics of the heat generating element rather than the control of the amount of air flow or water vapor transmission rate of an air permeable sheet. Hence, the moist heating device of the present invention is defined to have a heat generating element having the following heat generation characteristics. The heat generating element of the moist heating device of the invention has steam generating capability such that the amount of steam released per unit time reaches the maximum in 0.5 to 25 minutes from the start of heat generation. Applying the moist heating device having the heat generating element with such steam generating capability to a body surface of a wearer makes the wearer feel relaxed as will be demonstrated in Examples given later. In order to make the parasympathetic nervous system dominant, it is necessary to regulate the heat generation temperature of the moist heating device within a range that does not cause heat stimulus receptors to induce vasoconstriction. Therefore, if steam generation is delayed, it would take much time for a wearer to feel warmed, which makes it difficult for a wearer to feel satisfied.

Figure 4:
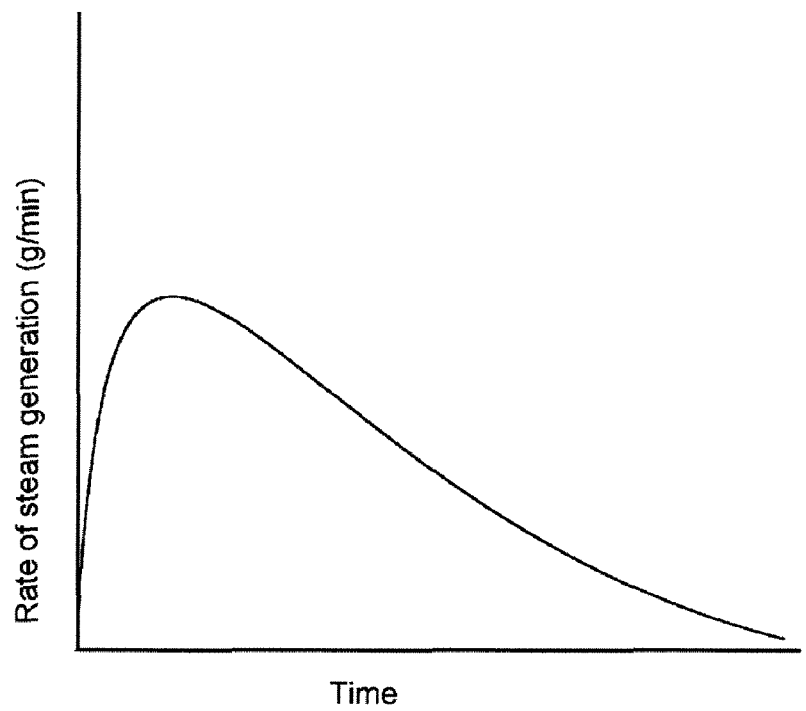
FIG. 4 is a graph of amount of steam released per unit time vs. time.

The amount of steam released from the heat generating element per unit time is a measure of ease of heat generation from the moist heating device. Forms of the heat generating element include a mixed powder and a molded sheet such as a sheet formed by a papermaking technique. The amount of steam released per unit time is measured as follows. The heat generating element taken out of a moist heating device is put on a heat generation temperature measuring instrument (JIS S4100) and made to start heat generation under conditions of 20° C.±2° C. and 50%±10% RH. Heat generation is accompanied by steam generation, whereby the moist heating device reduces in weight with time. The value obtained by subtracting the weight of the device after an elapse of a given time from the weight at the start of heat generation corresponds to the cumulative amount of steam generated by that time. There is thus prepared a curve representing the relationship of cumulative amount of steam vs. time. The curve is differentiated with respect to time to give a curve showing the amount of steam released from the heat generating element per unit time. An exemplary curve thus obtained is shown in FIG. 4. The weight is measured with an electronic balance.

The heat generating element of the moist heating device of the invention reaches the maximum capability of generating steam in terms of amount of steam released per unit time (hereinafter also referred to as "rate of steam generation" or "steam generation rate") in a given time from the start of heat generation. As a result of the inventors' investigation, it has been revealed that, when the time required for the moist heating device to reach the maximum rate of steam generation is in the range of from 0.5 to 25 minutes, the moist heating device promotes systemic blood circulation and raises peripheral temperatures more than a general disposable heat pack body warmer that produces little steam (i.e., dry heat), with the heating temperature and the application site being equal. It has also been revealed that the temperature increase outlasts the heat application for several tens of minutes. As a result, the moist heating device is capable of making a wearer feel relaxed. This is because, as has been found by the inventors, moist heat is transmitted at a higher rate than dry heat so that it is capable of increasing not only the skin temperature of the application site but the deep body temperature. It is assumed that a rise in temperature deep in the body stimulates the heat center, thereby to make the parasympathetic nervous system dominant. A moist heating device having a heat generating element that reaches the maximum rate of steam generation within less than 0.5 minutes is impracticable for application to the human body due to too high reactivity of its oxidizable metal component. On the other hand, a moist heating device having a heat generating element that reaches the maximum rate of steam generation after more than 25 minutes tends to make a wearer feel not warmed or tepid.

For example, as will be demonstrated in Examples given later, the moist heating device achieves superiority with significance to dry heat in evaluations of pupillary contraction rate, electrocardiographic R-R interval variability, total hemoglobin content, etc. when applied to the lower back or abdomen of a human subject, with the other conditions being equal. These evaluation items are widely recognized in physiological sciences as measures for judging which of parasympathetic and sympathetic nervous systems is dominant. While thermotherapy utilizing dry heat has been used conventionally, it has been first found by the inventors of the present invention that supplying moist heat using a moist heating device utilizing moist heat and possessing a means for allowing the parasympathetic nerves to dominate makes a user feel relaxed.

The moist heating device can have a controlled rate of steam generation from its heat generating element as appropriate to the type of the heat generating element. For instance, in the case where the heat generating element makes use of oxidation reaction of an oxidizable metal, the reaction rate is controlled by properly adjusting the amount of the reactants to be reacted in the heat generating element, the particle size of the reactant (if particulate), the rate of feeding the reactant, and so forth, thereby controlling the rate of steam generation.

The investigation by the present inventors has proved that the ratio of a water retaining agent to water in the heat generating element is largely influential on the amount of steam released. Existence of much water in the heat generating element is apt to increase the amount of steam generation. However, too much water makes the heat generating element too damp and hinders heat generation, resulting in the adverse effect of hindering steam generation. Hence, in the present invention, much water is incorporated into the heat generating element together with a water retaining agent so that water may be retained by the water retaining agent thereby to prevent the heat generating element itself from becoming too damp. As a result, the amount of steam released can be increased without being accompanied by hindrance to heat generation. According to the inventors' study, the time required for the heat generating element to reach the maximum rate of steam generation can easily be controlled within the above-specified range when the weight ratio of the total amount of water retaining agent to water in the heat generating element is preferably from 0.26 to 0.60, more preferably 0.30 to 0.50, even more preferably 0.30 to 0.45.

The weight ratio of an oxidizable metal to a reaction accelerator in the heat generating element has also been found influential on the amount of steam generation. Specifically, the time required for the heat generating element to reach the maximum rate of steam generation can easily be controlled within the above-specified range when the oxidizable metal to reaction accelerator weight ratio is preferably 2 to 25, more preferably 3 to 20, even more preferably 3 to 12. This seems to be because a reaction accelerator adheres around an oxidizable metal to form local batteries, by which the oxidation reaction is accelerated. The oxidizable metal/reaction accelerator weight ratio falling within the above-specified range, the duration of heat generation is extended sufficiently, and an appropriately rapid rise in heat generation temperature is obtained. With the weight ratio falling within the range, it is easy to raise the skin surface temperature at or above 38° C. as desired, to obtain a desired amount of steam generation, to reach an aimed temperature in a short time after a pillow type package of the moist heating device is opened, and to supply moderate moist heat for 3 hours or longer.

It is preferred that the moist heating device of the invention achieves not only the above-specified rate of steam generation but a cumulative amount of steam generation of 0.1 to 0.5 g, more preferably 0.1 to 0.3 g, per gram of the heat generating element in 30 minutes from the start of heat generation. When the cumulative amount of steam is in the above range, the device shows the effect of making the parasympathetic nervous system dominant. The cumulative amount of steam generated can be measured in the same manner as described above with respect to the rate of steam generation. The means for controlling the cumulative amount of steam generated within the recited range is the same as for the rate of steam generation.

While the water retaining agent to water weight ratio and the oxidizable metal to reaction accelerator weight ratio have been recited above, the compounding ratios of these materials are preferably as follows in order to secure a sufficient heat generation temperature and to generate a sufficient amount of steam. The compounding ratio of the water retaining agent is preferably 5% to 20%, more preferably 6% to 15%, by weight based on the weight of the heat generating element. The compounding ratio of the oxidizable metal is preferably 40% to 60%, more preferably 50% to 56%, by weight on the same basis. That of the reaction accelerator is preferably 1% to 10%, more preferably 2% to 6%, by weight on the same basis.

To supply a sufficient amount of moist heat to a wearer to bring the autonomic nervous system into a parasympathetic dominant state, the maximum rate of steam generation reached by the heat generating element is preferably in the range of from 0.01 to 0.1 g/min, more preferably 0.02 to 0.07 g/min. The rate of steam generation can be controlled within the recited range by compounding the oxidizable metal, water, the water retaining agent, and the like at the above-specified ratios.

The moist heating device according to the third aspect of the invention is characterized by having a long duration of steam generation in addition to having the above-described rate of steam generation. The duration of steam generation is preferably controlled by the water vapor transmission rate (hereinafter abbreviated as "WVTR") of a holder described later as measured in accordance with JIS Z0208 at 40° C. and 90% RH. The term "water vapor transmission rate (WVTR)" will hereinafter denote a value measured in the same method. Specifically, the holder is designed to have an air permeable portion with a WVTR of 150 to 2000 g/($m^2$·24 hr), preferably 400 to 1000 g/($m^2$·24 hr). By controlling the WVTR within that range and also by adjusting the water content of the heat generating element within the above-recited range, steam can be generated stably for a prolonged period of time. It follows that the moist heating device continues generating steam for a long period of time, preferably as long as 3 to 10 hours, more preferably 5 to 8 hours. It is preferred that the moist heating device has heat generating capability and steam generating capability such that, while the device is applied to a body surface, the body surface temperature may be maintained at a temperature of from 38° C. to lower than 42° C., more preferably from 38° C. to lower than 41° C., for a period of 3 to 10 hours, more preferably 5 to 8 hours. With the air permeable portion of the holder having a WVTR of the recited range, that portion takes the major role in controlling the air feed to the heat generating element of the moist heating device. The term "controlling the air feed" as used here means limiting the air feed to the heat generating element within a proper range. The control on the air feed makes it possible to cause the heat generating element to generate steam stably for an extended period of time. The body surface temperature measurement is made in the same manner as previously described.

The moist heating device of the third aspect is furthermore characterized by producing a large cumulative amount of steam. Specifically, the cumulative amount of steam released for 3 hours from the start of heat generation is preferably 0.5 to 12 mg/(3 hr·$cm^2$), more preferably 4 to 9 mg/(3 hr·$cm^2$). Such a large cumulative amount of steam can be reached by controlling the water content of the heat generating element within the above-specified range. As used herein, the terminology "cumulative amount of steam released or generated" refers to the total amount of steam that has been released in a period of three hours from initiation of oxidation reaction in the heat generating element of the moist heating device. The cumulative amount of steam released can be measured by the following method. A moist heating device 1 is placed in a closed chamber having a volume of 54000 cm$^3$ (36 cm (W)× 50 cm (L)×30 cm (H)) and having been conditioned at 20° C. and 40% RH in such a manner that the device is allowed to release steam in the chamber. An oxidation reaction is induced in the device, and the humidity of the air in the chamber is measured with a hygrometer to calculate the amount of water vapor generated after the commencement of the reaction. The cumulative amount of the water vapor generated up to 3 hours from the commencement of the reaction (i.e. the cumulative amount of steam released) is obtained.

A fourth aspect of the present invention is then described. Unless otherwise specified, the description of the first to third aspects applies appropriately to the fourth one. The fourth aspect relates to a moist heating device having the following steam generating capability. The steam generating capability of the moist heating device according to the fourth aspect is such that the skin surface temperature to which it is applied may be maintained at preferably 38° C. to 49° C., more preferably 38° C. to 43° C., for a period of 3 to 15 hours, preferably 3 to 10 hours, and that the cumulative amount of steam released therefrom is preferably 0.5 to 12 mg/(3 hr·cm$^2$), more preferably 4 to 9 mg/(3 hr·cm$^2$). Applying the moist heating device with such steam generating capability to a body surface markedly improves various physiological functions of a human body as will be demonstrated in Examples described infra. The skin surface temperature and the cumulative amount of steam released are measured in the same manner as described supra.

In order for the moist warming article to have the recited steam generating capability, the highest temperature reached by the moist warming article through chemical energy-induced heat generation is preferably 38° C. or higher. To prevent a low-temperature burn, the highest reachable temperature of the moist heating device is preferably 60° C. or lower. The highest temperature reached is measured in accordance with JIS S4100.

The moist heating device of the fourth aspect is used as applied to a bodily site, such as the lower back, the abdomen or a shoulder, with its steam release portion facing to the body portion. Warming the lower back, the abdomen or a shoulder with moist heat of the moist heating device of the fourth aspect increases not only the skin surface temperature of the application site but the deep body temperature. A rise in temperature deep in the body stimulates the heat center, whereby the autonomic nervous system becomes parasympathetic-dominant. It follows that the blood vessels dilate to promote the blood circulation and to raise the peripheral temperatures. A promoted blood circulation removes a pain producing substance, thereby resulting in alleviation or elimination of pain. Thus, the moist heating device is effective in not only elevating the temperature of the bodily site and improving the blood circulation where it is applied but also relieving or eliminating the pain of the bodily site, taking tiredness from muscles, decreasing muscle stiffness or soreness, and relieving nerve pain.

For example, as will be demonstrated in Examples given infra, application of the moist heating device to the lower back of a human body relieves or eliminates lower back pain, and application to the abdomen relieves or eliminates abdominal pain caused by constipation, diarrhea, etc. Application to the lower back and/or the abdomen also brings about improvement of visceral functions such as gastrointestinal functions and recovery from physical fatigue. While thermotherapy with dry heat has long been practiced, it is a fact first discovered by the inventors that various physiological functions of a human body are remarkably improved by using moist heat, particularly by supplying moist heat with the moist heating device having the above-mentioned steam generating ability.

How to control the steam generating ability of the moist heating device is decided appropriately according to the kind of chemical energy utilized. For example, the reaction rate is controlled by properly adjusting the amounts of reactants to be reacted in the steam generating element, the particle size of the reactant (if particulate), the rate of feeding the reactant, and so forth, thereby controlling the steam generating ability. It is also possible to control the steam generating ability by adjusting the amount of steam released from the steam generating element to be transferred to the body surface by interposing a moisture permeable sheet between the steam generating element and the body surface.

Figure 5:
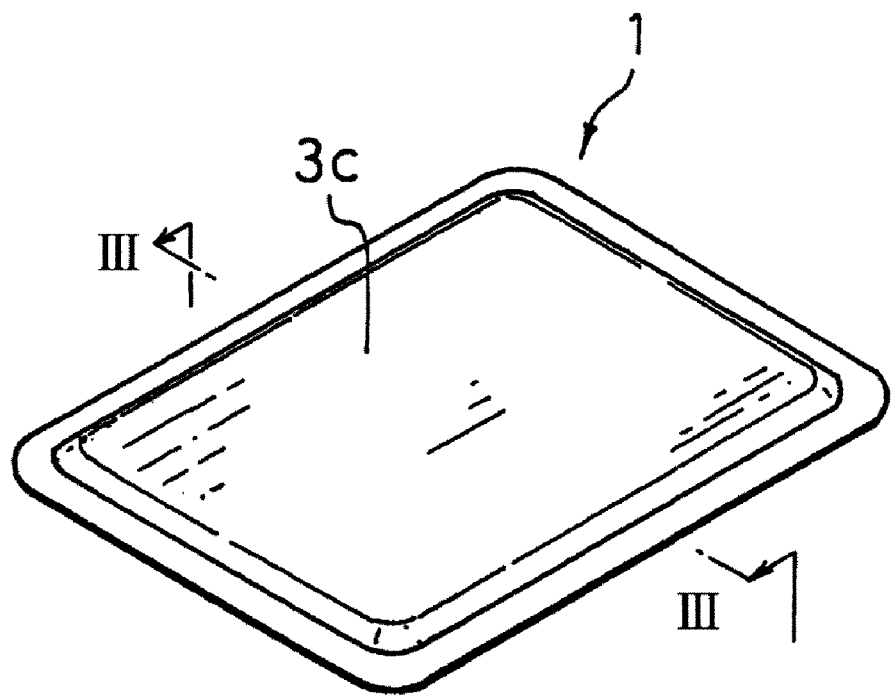
FIG. 5 is a perspective of a moist heating sheet as an embodiment of a physiology enhancing device according to the present invention.
Figure 6:
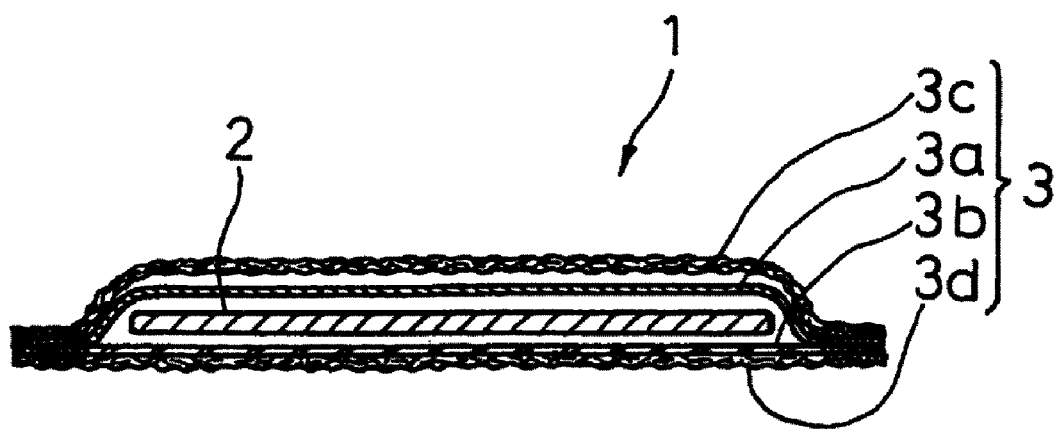
FIG. 6 is a cross-section of FIG. 5, taken along line III-III.

A preferred first embodiment common to the aforementioned first to fourth aspects of the present invention will be described by way of the accompanying drawing. FIG. 5 illustrates a moist heating sheet 1 as an embodiment of the present invention. FIG. 6 is a cross-section taken along line III-III in FIG. 5. The moist heating sheet 1 illustrated in FIG. 5 is flat and rectangular and includes a heat generating element 2 and a holder 3 for holding the heat generating element 2. The holder 3 is a flat bag and made of two or more sheets whose edges are joined together to make hallow inside. At least a part of the holder 3 is an air permeable portion having moisture permeability.

In the case where the heat generating element 2 is to generate heat by making use of oxidation reaction of an oxidizable metal, the heat generating element 2 is formed of a heat generative powder or sheet containing an oxidizable metal, a reaction accelerator, an electrolyte, and water. A sheet form is preferred to a powder form as a heat generating element 2 because, for one thing, a sheet form is easier to design to have a uniform temperature distribution. For another, a sheet form has high capability of supporting powder so that the heating element does not move to the movement of a human body and is therefore prevented from causing a low-temperature burn. As soon as the heat generating element 2 comes in contact with air, the oxidizable metal present in the heat generating element 2 starts being oxidized to generate heat. The water contained in the heat generating element 2 is heated by the generated heat into water vapor (steam) of prescribed temperature, which is released outside through the holder 3. The steam is released outside through the air permeable portion of the holder 3. The heat generating sheet is exemplified by a sheet formed by a papermaking technique and a laminate composed of a pair of sheets of paper, etc. and heat generative powder sandwiched therebetween. A sheet formed by a papermaking technique is preferred in view of better fit to a body surface and more uniform steam generation.

In the case of using a heat generating element 2 formed of heat generative powder, the heat generative powder is preferably composed of an oxidizable metal, a reaction accelerator, a water retaining agent, an electrolyte, and water. Of these materials those largely influential on the above specified steam generating ability of the moist heating sheet 1 were found, as a result of the inventors' study, to be the oxidizable metal, reaction accelerator and water retaining agent. Specifically, it is important that the heat generative powder contain preferably 20% to 50%, more preferably 25% to 40%, of an oxidizable metal, preferably 3% to 25%, more preferably 5% to 20%, of a reaction accelerator, and preferably 3% to 25%, more preferably 5% to 20%, of a water retaining agent, all by weight. With the contents of these materials falling within the recited respective preferred ranges, steam generating capability as desired is expected. It is also important for the heat generative powder to contain preferably 0.3% to 10%, more preferably 0.5% to 5%, of an electrolyte and preferably 20% to 70%, more preferably 30% to 60%, of water, all by weight, to develop steam generating capability as desired.

Where the heat generating element 2 is a heat generating sheet, the heat generating sheet is preferably formed of a fibrous sheet composed of an oxidizable metal, a reaction accelerator, a fibrous material, an electrolyte, and water. In other words, the heat generating sheet is preferably a water-wetted sheet containing an oxidizable metal, a reaction accelerator, a fibrous material, and an electrolyte. The heat generating sheet is more preferably a molded sheet containing an oxidizable metal, a reaction accelerator, and is a fibrous material and having incorporated therein an aqueous solution of an electrolyte.

In the case where the heat generating element 2 is a heat generating sheet, materials largely influential on the steam generating capability of the moist heating sheet 1 were found, as a result of the inventors' study, to be the oxidizable metal, the reaction accelerator, and the fibrous material. More specifically, it is important that the molded sheet contain preferably 60% to 90%, more preferably 70% to 85%, of the oxidizable metal, 5% to 25%, more preferably 8% to 15%, of the reaction accelerator, and 5% to 35%, more preferably 8% to 20%, of the fibrous material, all by weight. With the contents of these materials falling within the recited respective preferred ranges, you can expect steam generating capability as desired. The molded sheet is suitably prepared by a papermaking process as will be described later. The molded sheet as formed by papermaking and dried has a water content of 5% by weight or less.

Other important factors influential on the steam generating capability of the moist heating sheet 1 include the concentration of the aqueous electrolyte solution and the amount of the aqueous electrolyte solution in the heat generating sheet. Specifically, the concentration of the aqueous electrolyte solution in the heat generating sheet is preferably 1% to 15% by weight, more preferably 2% to 10% by weight. If the concentration is less than 1% by weight, the heat generating sheet can fail to provide a desired temperature. Appreciable further enhancement of the effects is not expected from concentrations higher than 15% by weight. The amount of the aqueous electrolyte solution to be added is preferably 30 to 80 parts by weight, more preferably 45 to 65 parts by weight, per 100 parts by weight of the molded sheet. Addition of less than 30 parts by weight can result in a failure to achieve a long duration of a desired temperature or a desired amount of steam generation. Addition of more than 80 parts by weight can result in a failure to obtain a desired temperature.

Other great factors influential on the steam generating capability of the moist heating sheet 1 include WVTR of the holder 3, irrespective of whether the heat generating element 2 is of powder form or sheet form. A preferred range of the WVTR of the holder is as stated previously. By using the heat generating element 2 containing the above-described components in the above-described compounding ratios and by using the holder 3 with the above-described WVTR, the moist heating sheet 1 can be designed to have the desired steam generating capability. With the air permeable portion of the holder 3 having a WVTR of the above-recited range, that portion takes the major role in controlling the air feed to the heat generating element 2 of the moist heating sheet 1. The term "controlling the air feed" as used here means limiting the air feed to the heat generating element 2 within a proper range. Such control on the air feed makes it feasible to cause the heat generating element to generate steam stably for an extended period of time.

In order to properly control the steam temperature and to secure a duration of steam generation at a desired temperature, it is preferred for the air permeable portion of the holder 3 to have an air permeance of 8000 to 15000 s/100 cm$^3$, more preferably 9000 to 12000 s/100 cm$^3$, as measured in accordance with JIS P8117. The term "air permeance" as used herein will hereinafter refer to a value measured in the same method. The air permeable portion of the holder 3 which has that range of permeance takes the major role in controlling the air feed to the heat generating element 2 of the moist heating sheet 1. The term "controlling" as used herein has the same meaning as defined above. For the same purpose it is preferred that the holder 3 has a steam release area of 0.001 to 0.25 m$^2$ more preferably 0.0025 to 0.04 m$^2$.

As will be described below, the air permeable portion of the holder 3 is formed of a moisture permeable film 3a and a nonwoven fabric 3c. Because the moisture permeable film 3a has a smaller WVTR and a larger air permeance than the nonwoven fabric 3c, the aforesaid WVTR and air permeance are chiefly decided by the moisture permeable film 3a. A larger air permeance means more difficulty for air to pass through.

As illustrated in FIGS. 5 and 6, the holder 3 of the moist heating sheet 1 of the first embodiment is a flat bag made by joining all the edges of the moisture permeable film 3a and a sparingly air permeable film 3b. That is, the moisture permeable film 3a and the sparingly moisture permeable film 3b each constitute a part of the holder. The holder 3 has the moisture permeable film 3a on its one side and the sparingly moisture impermeable film 3b on the opposite side. The moisture permeable film 3a allows passage of the steam generated from the heat generating element 2, whereas the sparingly moisture permeable film 3b lets through little steam. Therefore, steam is mostly released from only one side of the holder 3, i.e., the side of the moisture permeable film 3a. The WVTR and the air permeance of the moisture permeable film 3a being in the respective ranges specified previously, thus the moist heating sheet 1 exhibits the above specified steam generating capability.

As described, the moist heating sheet 1 of the first embodiment releases steam mostly from one side of the holder 3, i.e., the side of the moisture permeable film 3a. At the same time, air is fed mostly through one side of the holder 3, i.e., the side of the moisture permeable film 3a. As a result, air is supplied from the peripheral to the central portions of the moist heating sheet 1 of the first embodiment. Therefore, heat generation proceeds from the peripheral toward the central portions of the moist heating sheet 1 of the first embodiment. So configured, the moist heating sheet 1 of the first embodiment is capable of generating steam stably for a prolonged period of time.

The moisture permeable film 3a to be used is a film that allows passage of steam but hardly allows water to pass through. Such a film is exemplified by a microporous polyolefin film, which is well known for use as a moisture permeable backsheet of personal care absorbent products such as disposable diapers and sanitary napkins. Since steam is released outside through the moisture permeable film 3a as described above, the moist heating sheet 1 of the first embodiment is worn with the side of the moisture permeable film 3a facing the wearer's body. Then, a nonwoven fabric 3c having a soft hand, such as air-through nonwoven, is provided on the outer side of the moisture permeable film 3a to give an improved wearing comfort as shown in FIGS. 5 and 6. The nonwoven fabric 3c is also a part of the holder. While the moist heating sheet 1 is worn, it is the nonwoven fabric 3c that faces the body. The nonwoven fabric 3c is breathable to such an extent not to hinder passage of steam. The nonwoven fabric 3c is preferably water repellent so that it is prevented from being wetted to hinder passage of steam and to hinder entering of air.

While in the first embodiment the steam release side of the moist heating sheet 1 has a dual layer structure composed of the moisture permeable film 3a and the nonwoven fabric 3c, the structure of the steam release side is not limited thereto. The steam release side may have a single layer structure or a multilayer structure having three or more overlying sheets either joined together or not joined together. Where the steam release side is formed of a single layer sheet, a moisture permeable film such as a microporous polyolefin film can be used. Where the steam release side is formed of three or more sheets, the structure is exemplified by a combination of a moisture permeable film and two nonwoven fabrics of the same or different kinds.

The moist heating sheet 1 of the first embodiment supplies steam while being applied to a body surface with a sheet located between the heat generating element 2 and the body surface. In the first embodiment, it is the moisture permeable film 3a and the nonwoven fabric 3c that corresponds to the above-identified sheet. These members have a function of controlling air feed to the heat generating element 2 of the moist heating sheet 1 and a function of transferring the heat generated in the moist heating sheet 1 to the body surface. In the first embodiment, the total thickness of the moisture permeable film 3a and the nonwoven fabric 3c is preferably 0.05 to 1.5 mm in terms of stable air supply and efficient heat transfer to the skin (body surface). In particular, the moisture permeable film 3a and the nonwoven fabric 3c the total thickness of which is in the range recited are endowed mostly with the function of transferring the heat of the moist heating sheet 1 to the body surface. The moisture permeable film 3a and the nonwoven fabric 3c preferably have thicknesses of 0.01 to 0.1 mm and 0.03 to 0.5 mm, respectively, provided that their total thickness fall within the above range. The thickness is measured in accordance with JIS L1906 and/or L1096. That is, a thickness of a sample easily deformable under load is measured with a load of 2 kPa applied, and a thickness of a sample hardly deformable under load is measured with a load of 10 kPa applied.

The sparingly moisture permeable film 3b to be used is a film that allows passage of little water vapor or little water, such as a polyolefin film or a polyester film. To improve the texture of the moist heating sheet 1, a nonwoven fabric 3d, such as air-through nonwoven, is provided on the outer side of the sparingly moisture permeable film 3b as shown in FIG. 6.

As is obvious from the foregoing, the sheet forming the outer facing side of the holder 3 has a smaller value of WVTR or a greater value of air permeance than the sheet interposed between the heat generating element of the moist heating sheet 1 and a body surface. The WVTR or air permeance of the sheet defining the outer facing side refer to the overall WVTR or air permeance, respectively, of the sparingly moisture permeable film 3b and the nonwoven fabric 3d. The WVTR or air permeance of the sheet interposed between the heat generating element of the moist heating sheet 1 and a body surface refers to the overall WVTR or air permeance, respectively, of the moisture permeable film 3a and the nonwoven fabric 3c.

The materials constituting the heat generating sheet 2 which is formed of a heat generative powder will be described in detail. Examples of the oxidizable metal include powder or fiber of iron, aluminum, zinc, manganese, magnesium or calcium. Iron powder is preferred among them in view of ease in handling, safety, and production cost. When the oxidizable metal is powder, the oxidizable metal powder preferably has a particle size of 0.1 to 300 μm taking fixability onto a fibrous material and reaction controllability into consideration. For the same reasons, the oxidizable metal powder preferably contains at least 50% by weight of particles having a particle size of 0.1 to 150 nm.

The reaction accelerator is preferably selected from materials serving as a water retaining agent and also having a function as an agent for retaining and supplying oxygen to the oxidizable metal. Examples of such materials include activated carbon (including coconut shell charcoal, charcoal powder, bituminous coal, peat, and lignite), carbon black, acetylene black, graphite, zeolite, pearlite, and silica. Preferred of them is activated carbon in view of its water retaining capability, oxygen feeding capability, and catalyzing ability. The reaction accelerator preferably has a particle size ranging from 0.1 to 500 μm for effective contact with the oxidizable metal. For the same reason, it is preferred for the reaction accelerator to contain at least 50% by weight of particles having a particle size of 0.1 to 200 μm.

Examples of the water retaining agent include fibrous materials, water absorbent polymers, vermiculite, calcium silicate, silica gel, and alumina. Preferred of them are absorbent polymers in view of their high water retention capacity and high productivity.

Examples of useful electrolytes include sulfates, carbonates, chlorides, and hydroxides of alkali metals, alkaline earth metals or transition metals. Preferred of them are chlorides of alkali metals, alkaline earth metals or transition metals for their electrical conductivity, chemical stability, and production economy. Sodium chloride, potassium chloride, calcium chloride, magnesium chloride, iron (I) chloride, and iron (II) chloride are particularly preferred.

In the case where the heat generating element 2 has a powder form, it is obtained by uniformly mixing the constituent materials. It is particularly preferred to prepare the heat generating element 2 by first uniformly mixing a water retaining agent such as a superabsorbent polymer and an oxidizable metal, adding an aqueous electrolyte solution thereto to cause the oxidizable metal to adhere to the surface of the water retaining agent, and then adding the other materials including a reaction accelerator. The heat generating element 2 so prepared shows a more rapid rise of oxidation reaction, which makes it easier to reach the maximum rate of steam generation within the above-recited range of time.

In the case where the heat generating element 2 is a heat generating sheet, the method of making the heat generating sheet is not limited. Since the heat generating sheet is, as mentioned above, a molded sheet containing an oxidizable metal, a reaction accelerator, and a fibrous material and having an aqueous electrolyte solution incorporated therein, it is obtained by first forming a molded sheet containing the oxidizable metal, the reaction accelerator, and the fibrous material and then adding the aqueous electrolyte solution to the sheet. The molded sheet can be prepared by, for example, the wet papermaking process disclosed in commonly assigned JP 2003-102761A or by extrusion using a die coater. The wet papermaking process is preferred from the standpoint of production cost and productivity. Papermaking machines useful for wet papermaking include a cylinder paper machine, a foundrinier paper machine, a short-wire paper machine, and a twin-wire paper machine. The slurry used for wet papermaking contains the oxidizable metal, reaction accelerator, fibrous material, and water and has a concentration preferably of 0.05% to 15% by weight, more preferably of 5% to 12% by weight.

Any natural or synthetic fibers can be used as the fibrous material without limitation. Examples of the natural fibers include plant fibers, such as cotton, kapok fiber, wood pulp, non-wood pulp, peanut protein fiber, corn protein fiber, soybean protein fiber, mannan fiber, rubber fiber, hemp, Manila fiber, sisal fiber, New Zealand flax, Luo Buma, coconut, rush, and straw; animal fibers, such as wool, goat hair, mohair cashmere, alpaca, angora, camel, vicuna, silk, plumage, down, small feather, alginate fiber, chitin fiber, and casein fiber; and mineral fibers, such as asbestos. Examples of the synthetic fibers include semi-synthetic ones, such as rayon, viscous rayon, cuprammonium, cellulose acetate, cellulose triacetate, oxidized cellulose acetate, promix, and chlorinated rubber; and fibers of synthetic polymers, such as nylon, aramid, polyvinyl alcohol, polyvinyl chloride, polyvinylidene chloride, polyesters (e.g., polyethylene terephthalate), polyacrylonitrile, acrylic resins, polyethylene, polypropylene, polystyrene, and polyurethane. Among these fibrous materials particularly preferred are wood pulp, cotton, polyethylene fiber, and polyester fiber in view of their fixing capabilities for the oxidizable metal and the reaction accelerator, flexibility, oxygen permeability, and sheet shape retention of the resulting heat generating element 2, and the cost of production. Wood pulp and cotton have the capability to support and immobilize solids such as iron powder. The fibrous material preferably has an average fiber length of 0.1 to 50 mm, more preferably 0.2 to 20 mm, to secure strength of the heat generating sheet and dispersibility of the fibrous material in water.

A combined use of a natural fiber such as wood pulp and a synthetic fiber such as polyethylene fiber or polyester fiber (especially thermoplastic resin fiber) is particularly preferred; for an increase of an oxidizable metal can be prevented from causing a reduction in mechanical strength of the resulting molded sheet. In this case, the mixing ratio of a natural fiber to a synthetic fiber is preferably such that the proportion of a synthetic fiber is 0.1 to 20 parts by weight, more preferably 0.5 to 10 parts by weight, per 100 parts by weight of a natural fiber.

It is preferred for the fibrous material to have a CSF (Canadian Standard Freeness; JIS P8121) of 600 ml or less, more preferably 450 ml or less. With such a freeness, the fibrous material has satisfactory ability to fix and hold the oxidizable metal, assuring satisfactory heat generation performance of the heat generating sheet. Furthermore, it is easy to control the breaking length defined later within a specific range recited later. As a result, fall-off of the oxidizable metal from the heat generating sheet can be prevented, and the heat generating sheet exhibits adequate mechanical strength. It is desirable for the fibrous material to have as low a CSF as possible. In carrying out papermaking using a slurry containing ordinary pulp fiber as a sole fibrous material and having high contents of other components, the CSF is preferably 100 ml or higher to secure satisfactory drainage and dewatering to provide a heat generating sheet with a uniform thickness. Moreover, molding defects such as bursting of blisters on drying are hardly experienced. Since the proportion of the components other than the fibrous material in the heat generating sheet is relatively high, the slurry shows satisfactory drainage to provide a heat generating sheet 2 with a uniform thickness. A lower CSF indicates a higher fibril content, and a higher fibril content secures better fixation of the components other than the fibrous material on the fibrous material, which results in high sheet strength. The CSF of a fibrous material can be controlled by, for example, the degree of beating. The CSF may also be adjusted by blending fibers different in CSF.

The molded sheet obtained by papermaking is dewatered preferably to a water content of 70% or less (by weight, hereinafter the same), more preferably 60% or less, for assuring shape retention and mechanical strength after sheet formation. Dewatering of the molded sheet after sheet formation is carried out by, for example, suction, application of pressurized air or pressing with a pressure roll or a pressure plate.

After dewatering, the molded sheet is preferably dried by heating. The heating temperature is preferably 60° C. to 300° C., more preferably 80° C. to 250° C. The water content of the molded sheet after drying is preferably 20% or less, more preferably 10% or less. The dewatering step and/or the drying step of the molded sheet are preferably conducted in an inert gas atmosphere to prevent oxidation of the oxidizable metal. Nevertheless, because the molded sheet is free from an electrolyte acting as an oxidation promoter, these steps may be performed in an ordinary air atmosphere if desired, which is advantageous in enabling simplification of equipment. The molded sheet after the drying contains the oxidizable metal, the reaction accelerator, and the fibrous material. Preferably, the molded sheet after the drying contains 60% to 85% by weight, more preferably 70% to 80% by weight, of the oxidizable metal, 5% to 25% by weight, more preferably 8% to 15% by weight, of the reaction accelerator, and 5% to 35% by weight, more preferably 10% to 20% by weight, of the fibrous material.

The thickness of the resulting molded sheet (i.e., the heat generating sheet before addition of water) is preferably 0.1 to 2 mm, more preferably 0.15 to 1.5 mm per sheet, to have both mechanical strength and flexibility for a good fit to an application site of the body. The recited thickness is also preferred in terms of uniformity of heat generation distribution. Moreover, when applied to a wearer's body, the moist heating sheet 1 with the recited thickness is practically inconspicuous from outside the wearer's clothing. For the same reasons, the grammage of the molded sheet is preferably 10 to 1000 $g/m^2$ more preferably 50 to 600 $g/m^2$, even more preferably 100 to 500 $g/m^2$.

A plurality of the molded sheets can be used as stacked on each other. The molded sheet can be used as folded, and a plurality of the folded sheets may be stacked on each other. The weight ratio of the molded sheet to the area of the moist heating sheet 1 is preferably 0.03 $g/cm^2$ to 0.17 $g/cm^2$, more preferably 0.06 $g/cm^2$ to 0.14 $g/cm^2$, to attain a desired temperature duration and a good fit without inviting manufacturing disadvantages. For the same reason, the weight to unit area ratio of the oxidizable metal is preferably 0.02 $g/cm^2$ to 0.14 $g/cm^2$, more preferably 0.04 $g/cm^2$ to 0.12 $g/cm^2$.

To prevent fall-off of the oxidizable metal from the molded sheet during use of the moist heating sheet 1 and to maintain the flexibility of the molded sheet, the molded sheet preferably has a breaking length of 200 to 4000 m, more preferably 200 to 3000 m, as measured in accordance with JIS P8113 (hereinafter the same). A molded sheet having a breaking length falling within the recited range is obtained easily by using a fibrous material having the above-specified CSF.

The molded sheet thus prepared is then impregnated with an aqueous electrolyte solution to obtain the heat generating sheet. This step is desirably conducted in an inert gas atmosphere of nitrogen, argon, etc. Impregnation with an aqueous electrolyte solution can be carried out by spraying, brush coating, dip coating, gravure coating, reverse coating, doctor blade coating or the like method. The electrolyte concentration of the aqueous solution and the amount of the solution to be added are adjusted so that the contents of the electrolyte and water in the resulting heat generating sheet may fall within the respective ranges recited previously.

If desired, the heat generating element 2 formed of the heat generating sheet can contain additives commonly used in papermaking with no particular restriction. Such additives include flocculants, sizes, colorants, strengthening agents, yield improvers, loading materials, thickeners, pH control agents, and bulking agents.

The heat generating element 2, either of powder form or sheet form, is distinctly different from the heat generative material used in commonly available disposable heat pack body warmers in that it contains much more water. More specifically, the amount of water present in the heat generating element 2 is on a high water content level, preferably as large as 30% to 60%, more preferably 32% to 45%, by weight based on the weight of the heat generating element 2 excluding water and the electrolyte. This is to generate a sufficient amount of steam within a given period of time from the start of heat generation. Designed to supply dry heat but not to generate steam (not to supply moist heat), common disposable heat pack body warmers have a low water content level.

The heat generating element 2, whether being of powder form or sheet form, is held in the holder 3 to provide the moist heating sheet 1. The moist heating sheet 1 is preferably packaged in a wrapper made of an oxygen barrier material to be supplied as an individually packaged moist heating sheet. On use, the moist heating sheet 1 is taken out of the package, whereupon the oxidizable metal contained in the moist heating sheet 1 reacts with oxygen in air to start heat generation and, at the same time, steam generation. Materials of such an oxygen barrier wrapper preferably include those having an oxygen transmission rate (ASTM D-3985) of 10 $cm^3 \cdot mm/(m^2 \cdot day \cdot MPa)$ or lower, more preferably 2 $cm^3 \cdot mm/(m^2 \cdot day \cdot MPa)$ or lower, and those having an oxygen transmission rate (JIS K7126B, 20° C., 0% RH) of 10 $cc/(m^2 \cdot 24 \, hr \cdot atm)$ or less, such as an ethylene-vinyl alcohol copolymer and polyacrylonitrile.

The package containing the moist heating sheet 1 is preferably labeled to indicate that the moist heating sheet 1 is for enhancement of human physiology. For example, the package may be labeled to the effect that application to any body site brings about an increase in deep temperature at the application site which will result in an increased blood flow and accelerated blood circulation or an increase in peripheral temperature which will alleviate oversensitivity to cold or nerve pain. The package may be labeled to the effect that application to the lower back reduces or eliminates lower back pain or that application to the abdomen reduces or eliminates abdominal pain or constipation or that application to the lower back and/or the abdomen improves the gastrointestinal functions and helps recover from fatigue. Consumers will be informed by this labeling that the moist heating sheet of the present invention achieves physiology enhancing effects that have heretofore been impossible with conventionally known disposable body warmers. Thus, the good value of the improved performance of the present invention will easily be recognized by consumers. The labeling can contain any kind of information means for conveying information about the improved performance to consumers, including signs and graphics as well as characters. The labeling may contain information to the effect that the product of the present invention is superior to other commercial products. In addition to, or in place of, the labeling on the package, instructions containing the contents of the labeling may be put in the package together with the moist heating sheet 1. The labeling may be printed directly on the moist heating sheet 1.

In addition to the above-described labeling, it is also preferred that the package containing the moist heating sheet 1 is labeled to the effect that the moist heating sheet is for relaxing a wearer's body. For example, the package may be labeled such that application of the moist heating device 1 to the lower back or abdomen will give a wearer a gentle feeling of relaxation as well as a feeling of being warmed. Consumers will thus be informed by this labeling that the present invention achieves relaxing effects that have heretofore been impossible with conventionally known disposable body warmers.

The moist heating sheet 1 of the first embodiment can be applied to a human body by putting into an attachment belt shown in FIGS. 7(*a*) and 7(*b*) and attaching the belt around the body. The attachment belt 10 shown in FIGS. 7(*a*) and 7(*b*) has a rectangular holding part 12 in the center thereof which can hold and support the moist heating sheet 1 and a pair of arms, a first arm 13*a* and a second arm 13*b*, extending from the opposing sides of the holding part 12. The first arm 13*a* and the second arm 13*b* are symmetrical. The first and the second arms 13*a* and 13*b* make an angle θ with a horizontal line H extending in the longitudinal direction of the attachment belt 10.

A fastening means 15, such as a hook member of a hook-and-loop mechanical fastener, is attached to the body-facing side (the paper face of FIG. 7(*a*)) of the distal end of the first arm 13*a*, while a landing member (not shown) on which the fastening means 15 is fixed, such as a loop member of a hook-and-loop mechanical fastener, is attached to the outer side (the side opposite to the paper face of FIG. 7(*a*)) of the second arm 13*b*.

The first and the second arms 13*a* and 13*b* are each composed of a proximal part 14*a* nearer to the holding part 12 and a distal free end part 14*b* nearer to the arm end. The proximal part 14*a* has its width decreasing toward the free end part 14*b*. The proximal part 14*a* and the free end part 14*b* connect to each other at the position where the width of the proximal part 14*a* no more decreases. The proximal part 14*a* preferably has stretchability in both the extending direction of the arms 13*a* and 13*b* and the direction perpendicular to that direction (indicated by the two-headed arrows in FIG. 7(*a*)). For that purpose, the proximal part 14*a* is preferably made of two-way stretchable fabric.

An outer panel 21 is preferably made of fabric with an desirable feel to the touch. It is preferred for the outer panel 21 to have sufficient air permeability. The outer panel 21 can be made of, for example, tricot fabric. Similarly, a first skin facing panel 22 and a second skin facing panel 23 are preferably made of fabric with an desirable feel to the touch. Moreover, it is preferred that the first and the second skin facing panels 22 and 23 are made of materials having sufficient water vapor permeability. Such materials include knitted mesh fabric.

The holding part 12 is formed of three panels 21, 22, and 23, sewed together to make a bag. The outer panel 21 is provided on the outer side of the attachment belt 10 and has a rectangular shape. The first skin facing panel 22 and the second skin facing panel 23 are provided on the skin facing side of the attachment belt 10 and have a rectangular shape. All the first and the second skin facing panels 22 and 23 and the outer panel 21 have the same length in the horizontal direction. The width of the two skin facing panels 22 and 23 is smaller than that of the outer panel 21 in the vertical direction. The first skin facing panel 22 is sewed together with the outer panel 21 along its upper side and both lateral sides. The second skin facing panel 23 is sewed together with the outer panel 21 along its lower side and both lateral sides. The lower part of the first skin facing panel 22 and the upper part of the second skin facing panel 23 overlap with each other, and the lower edge 22*a* of the first skin facing panel 22 and the upper edge 23*a* of the second skin facing panel 23 are free edges. Thus, the holding part 12 has an opening 24 formed on its skin facing side. The opening 24 extends transversely across the holding part 2. The moist heating sheet 1 is put inside the holding part 12 through the opening 24. As stated, the lower part of the first skin facing panel 22 and the upper part of the second skin facing panel 23 overlap with each other so that the moist heating sheet 1 once put into the holding part 12 hardly comes out of the holding part 12 and is stably held in the holding part 12. The size of the opening 24 is large and easy to open thereby easily putting in and taking out the moist heating sheet 1.

The moist warming sheet 1 held in the attachment belt 10 is applied to, e.g., the lower back or the abdomen of a human body as illustrated in FIGS. 8(*a*) and 8(*b*). It is applicable to an arm, a leg or a shoulder by using a holder of another design. To attach the belt to the body, the attachment belt 10 is wound around the waist, and the fastening means (not shown) provided on the first arm 13*a* is fastened to the landing member (not shown) provided to the second arm 13*b*. In that case, the moist heating sheet 1 faces the body surface via the water vapor-permeable first and second skin facing panels 22 and 23 of the attachment belt 10. In that mode of application, the sheet adapted to be interposed between the heat generating element 2 of the moist heating sheet 1 and a body surface is the above-described moisture permeable film 3*a* and the nonwoven fabric 3*c* of the holder and the first and second skin facing sheets 22 and 23 of the attachment belt. Accordingly, it is preferred that the total thickness of these members is in the range of from 0.05 to 1.5 mm for the previously stated reasons. With the total thickness falling within that range, each of the first and second skin facing sheets 22 and 23 preferably has a thickness of 1.4 mm or smaller.

Figure 9:
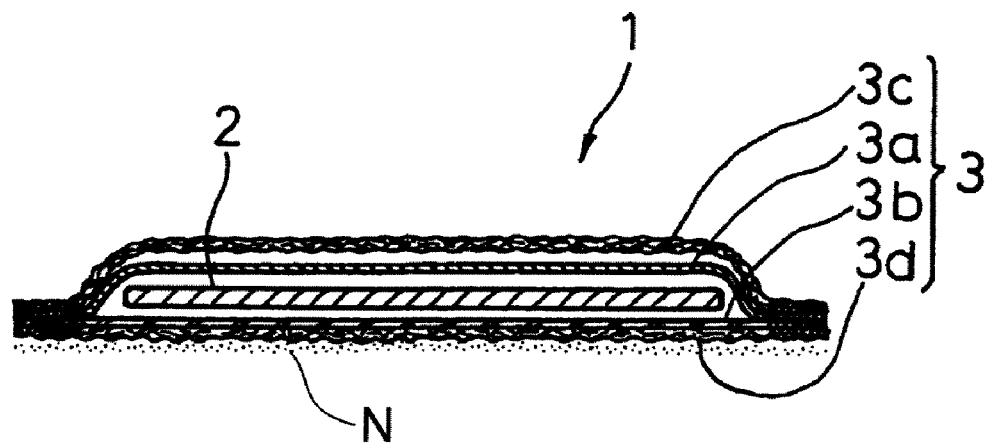
FIG. 9 is a cross-section of another embodiment of a physiology enhancing device according to the present invention (corresponding to FIG. 6).

In a modified mode of application, the moist heating sheet 1 may be brought in direct contact with a body surface. In this case, the moist heating sheet 1 has a pressure sensitive adhesive N applied to its side of the sparingly moisture permeable film 3*b* as illustrated in FIG. 9. The moist heating sheet 1 is adhered to the skin facing side of the holding part 12 of the attachment belt 10 via the adhesive N. In other words, the moist heating sheet 1 is not put in the holding part 12. The attachment belt 10 thus having the moist heating sheet 1 adhered thereto is wound around the body. Alternatively, the moist heating sheet 1 may directly be attached to a wearer's undergarment via the adhesive N.

A second preferred embodiment common to the aforementioned first to fourth aspects of the present invention will then be described with reference to FIGS. 10 and 11. The description on the first embodiment applies to the second embodiment described hereunder unless otherwise specified. The moist heating sheet 1 of the second embodiment is used as fixed to a wearer's body. The expression "fixed to a wearer's body" as used herein is intended to mean not only being fixed directly to the skin but also being fixed to a wearer's undergarment.

The moist heating sheet 1 is oblong and flat. The moist heating sheet 1 includes a heat generating element 2 and a holder 3 in which the heat generating element 2 is held. The holder 3 is a flat bag having a closed space formed by joining a plurality of sheets along a closed loop of a joint 4. The closed space is a holding part 5 in which the heat generating element 2 is put.

Figure 11:
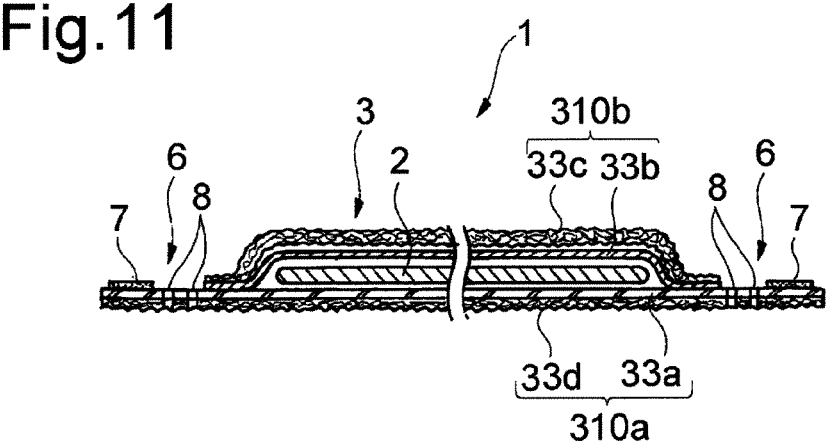
FIG. 11 is a cross-section of FIG. 10, taken along line II-II.

As illustrated in FIG. 11, the holder 3 includes a first moisture permeable sheet 33*a* and a second moisture permeable sheet 33*b* joined together along the joint 4. As illustrated, a nonwoven fabric 33*c* having a pleasant feel to the touch is provided on the outer side of the second moisture permeable sheet 33*b* to improve the comfort of wearing the moist heating sheet 1, and nonwoven fabric 33*d* is provided on the outer side of the first moisture permeable sheet 33*a* to improve the feel of the moist heating sheet 1. The second moisture permeable sheet 33*b* and the nonwoven fabric 33*c* have practically the same size. The first moisture permeable sheet 33*a* and the nonwoven fabric 33*d* may be joined together only along their perimeters or via joints discretely arranged over their area, and so may the second moisture permeable sheet 33*b* and the nonwoven fabric 33*c*. The first moisture permeable sheet 33*a* and the nonwoven fabric 33*d* in combination serve as a first air permeable layer 310*a* that is to be located farther from the wearer's skin while worn. The second moisture permeable sheet 33*b* and the nonwoven fabric 33*c* in combination serve as a second air permeable layer 310*b* that is to be located closer to the wearer's skin while worn. That is, the moist heating sheet 1 of the second embodiment has air permeability on both sides thereof and is designed to be fixedly attached to a bodily side of a wearer with its side of the second moisture permeable sheet 33*b* and the nonwoven fabric 33*c* facing the skin. While in the present embodiment the first air permeable layer 310*a* is composed of the first moisture permeable sheet 33*a* and the nonwoven fabric 33*d*, and the second air permeable layer 310*b* is composed of the second moisture permeable sheet 33*b* and the nonwoven fabric 33*c*, the first and second air permeable layers 310*a* and 310*b* may be formed solely of the moisture permeable sheet 33*a* and 33*b*, respectively.

Figure 12:
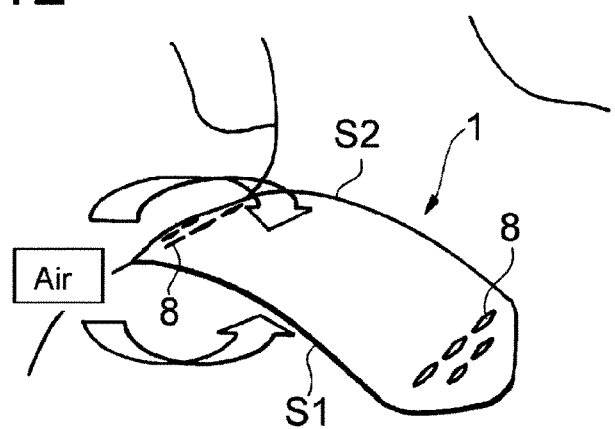
FIG. 12 illustrates a mode of use of the physiology enhancing device shown in FIG. 10.

The holder 3 has opposing side edges S1 and S2 that extend in the longitudinal direction and opposing end edges E1 and E2 that extend in the width direction. The side edge S1 is curved outward with respect to the longitudinal centerline of the holder 3, while the side edge S2 is curved inward with respect to the longitudinal centerline of the holder 3. Each of the end edges E1 and E2 is curved outward. The side edges S1 and S2 and end edges E1 and E2 are smoothly connected together to make up an elongated circle as a whole. The moist heating sheet 1 having the so shaped holder is a good fit when applied to a shoulder of a human body as illustrated in FIG. 12. In this mode of application, the moist heating sheet 1 is attached with the side edge S2 positioned nearer to the neck, and the side edge S1 farther from the neck as illustrated in FIG. 12.

Figure 10:
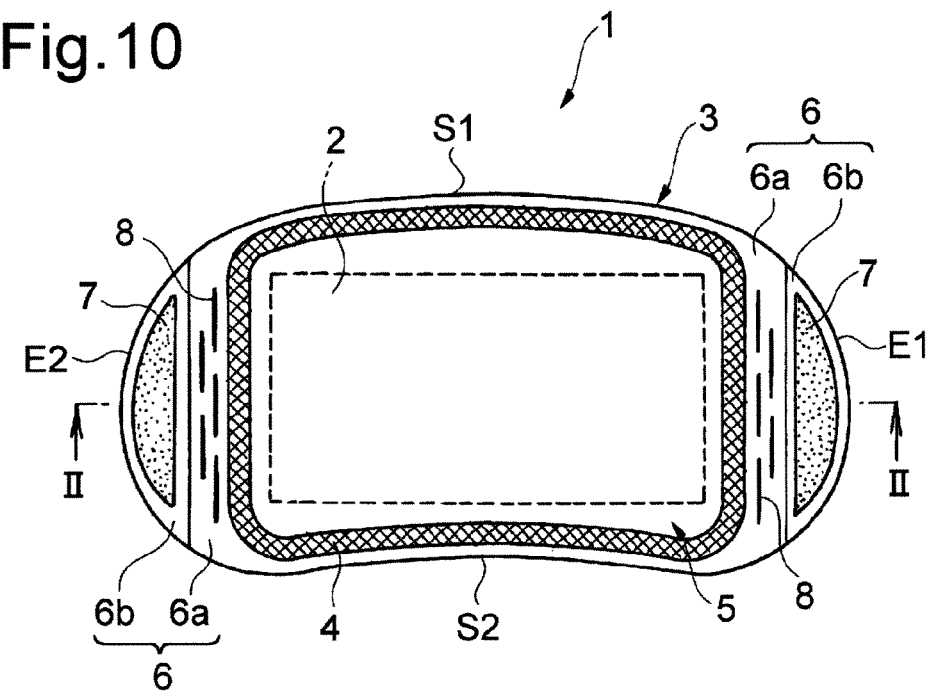
FIG. 10 is a plan of still another embodiment of a physiology enhancing device according to the present invention.

Back to FIGS. 10 and 11, the first moisture permeable sheet 33*a* and the nonwoven fabric 33*d* extend outward from the joint 4 that surrounds the holding part 5 in the longitudinal direction of the holder 3 to form a pair of ears 6. Each ear 6 is composed of a proximal portion 6*a* nearer to the joint 4 and a distal portion 6*b* farther from the joint 4 and adjoining the proximal portion 6*a*.

Each distal portion 6*b* is provided with an attachment part 7 for fixedly attaching the moist heating sheet 1 to a wearer's body. Each attachment part 7 is disposed at a position outboard of the holding part 5 of the heat generating element 2 on the side of the second moisture permeable sheet, i.e., on the side closer to the skin. There are provided two attachment parts 7, each of which is located on the longitudinal centerline of the holder 3. The positions of the attachment parts 7 in the holder 3 are the most distant possible from each other.

Various means for fixing the moist heating sheet 1 onto a user's body can be used as the attachment part 7. Typically, a pressure-sensitive adhesive is applied to the distal portion 6*b* to make the attachment part 7. The adhesive is chosen from those commonly employed in the art, such as rubbery resins, acrylic resins, and vinyl acetate resins. It is preferred to use a non-residue type adhesive resin.

In the heat generating element 2, the region between the holding part 5 and the attachment part 7, namely the proximal portion 6a is extensible. The proximal portion 6a is extensible in the direction connecting the two attachment parts 7, i.e., the direction of the longitudinal centerline L. In the second embodiment, the proximal portion 6a is made extensible by cutting a number of slits 8 therein. The details are as follows.

Each slit 8 cut in the proximal portion 6a extends in the direction crossing the longitudinal centerline L. The slits 8 open wider on pulling the moist heating sheet 1 in opposite longitudinal directions, whereby the proximal portion 6a extends in these directions. When the moist heating sheet 1 is attached to the body of a wearer, for example, as illustrated in FIG. 12, the proximal portion 6a extends in conformity to the wearer's movement. As a result, a pulling sensation of the skin of the application site can be prevented, and the attachment part 7 is prevented from coming off the skin. While in FIG. 10 the slits 8 extend perpendicularly to the longitudinal centerline of the moist heating sheet 1, the crossing angles between the slits 8 and the longitudinal centerline do not always need to be 90 degrees. Nevertheless, the closer to 90 degrees the crossing angles, the more preferred for the extensibility of the proximal portion 6a.

The slits 8 in each proximal portion 6a are arranged in double file at regular intervals. The slits in one line and those in the other line are out of alignment by half pitch. To secure sufficient extensibility of the proximal portion 6a, the length of each slit 8 is preferably 5 to 50 mm, more preferably 10 to 30 mm. For the same reason, the interval of the slits in each line is preferably 2 to 10 mm, more preferably 3 to 7 mm, and the distance between the two lines is preferably 2 to 10 mm, more preferably 3 to 7 mm.

As described previously, the moist heating sheet 1 of the second embodiment is air permeable on its both sides, that is, it lets in air from both the side closer to the skin and the side farther from the skin. In the second embodiment, it is preferred to select the moisture permeable sheets 33a and 33b so that the WVTR of the first air permeable layer 310a (taken as A ($g/m^2 \cdot 24$ hr)) and that of the second air permeable layer 310b (taken as B ($g/m^2 \cdot 24$ hr)) may satisfy the following equations (1) to (3):

$$A+(B/3)=200 \sim 500 \text{ g/(m}^2 \cdot 24 \text{ hr)} \quad (1)$$

$$A+B=200 \sim 700 \text{ g/(m}^2 \cdot 24 \text{ hr)} \quad (2)$$

$$B=100 \sim 450 \text{ g/(m}^2 \cdot 24 \text{ hr)} \quad (3)$$

Equation (1) is relative to the average temperature of the moist heating sheet 1. Seeing that the moist heating sheet 1 has air permeability on both sides thereof, the overall air permeability of the sheet 1 is the sum of the WVTR of the first air permeable layer 310a and that of the second air permeable layer 310b. However, because the second moisture permeable sheet 33b, which is positioned on the side closer to the skin, has a part thereof brought into contact with the wearer's body, it is difficult for the sheet to let in air through the entire area thereof. Then, in the second embodiment, the ratio of the area of the second air permeable layer 310b that allows air to flow, i.e., the ratio of the area that contributes to air flow, is regarded to be one-third of the entire area of the second air permeable layer 310b in average over the time of use of the moist heating sheet 1. That is the reason the WVTR of the second air permeable layer 10b (i.e. B) is multiplied by a factor of ⅓. The lower limit of equation (1) is 200 g/($m^2 \cdot 24$ hr) so as to obtain a heat generation temperature enough for a wearer to feel warmed. The upper limit of equation (1) is 500 g/($m^2 \cdot 24$ hr) to prevent excessive air feed into the moist heating sheet 1 thereby avoiding an excessive rise of heat generation temperature. In order to control the average skin temperature within a range of from 38° C. to lower than 42° C. and to control the average temperature of the moist heating sheet 1 within a range of from 40° C. to 45° C., the value of equation (1) is preferably 200 to 500 g/($m^2 \cdot 24$ hr), more preferably 200 to 350 g/($m^2 \cdot 24$ hr).

Equation (2) is pertinent to the highest temperature of the moist heating sheet 1. The average ratio of the area contributory to air feed to the entire area of the second air permeable layer 310b, which is positioned on the side closer to the skin, is one-third as explained above with reference to equation (1). Nevertheless, cases can occur in which air flows in through the entire area of both the first and second air permeable layers 310a and 310b while the moist heating sheet 1 is used. In such cases, the temperature of the moist heating sheet 1 can rise abruptly even under the average temperature control by equation (1). Equation (2) is to avoid such an abrupt temperature rise, in which the overall WVTR of the moist heating sheet 1, i.e., the sum of the WVTR of the first air permeable layer 310a and the second air permeable layer 310b is limited to control the highest temperature of the moist heating sheet 1. With the upper limit of equation (2) set at 700 g/($M^2 \cdot 24$ hr), an abrupt temperature rise can be avoided. The lower limit of equation (2) is 200 g/($m^2 \cdot 24$ hr) to obtain a heat generation temperature enough to make the wearer feel warmed. In order to control the highest temperature below 50° C. if any abrupt temperature rise occurs, the value of equation (2) is preferably 200 to 500 g/($m^2 \cdot 24$ hr).

Unlike equations (1) and (2), equation (3) is to specify only the WVTR of the second air permeable layer 310b, which is located on the side closer to the skin; equation (3) relates to fluctuation in temperature of the moist heating sheet 1. The moist heating sheet 1 of the second embodiment induces moderate fluctuations in heat generation temperature by taking advantage of the variation in air feed through the second air permeable layer 310b, which is located on the side closer to the skin, while securing sufficient air flow through the first air permeable layer 310a, which is located on the side farther from the skin. Accordingly, the width of the fluctuations in heat generation temperature can be adjusted by properly controlling the WVTR of the second air permeable layer 310b. With the lower limit of equation (3) at 100 g/($m^2 \cdot 24$ hr), the width of fluctuations in heat generation temperature is prevented from becoming too small so as to give a wearer a long-lasting feeling of warmth. With the upper limit of equation (3) at 450 g/($m^2 \cdot 24$ hr), the fluctuation width is prevented from becoming too large so as to prevent an abrupt rise in temperature. The value of equation (3) is preferably 100 to 450 g/($m^2 \cdot 24$ hr), more preferably 250 to 400 g/($m^2 \cdot 24$ hr).

While the WVTR of the first air permeable layer 310a itself is not particularly limited, it is preferably 100 to 400 g/($m^2 \cdot 24$ hr), more preferably 150 to 300 g/($m^2 \cdot 24$ hr), in relation to equations (1) through (3). It is preferred that the WVTR of the second air permeable layer 310b is smaller than that of the first air permeable layer 310a. Similarly, it is preferred that the air permeance value of the second air permeable layer 310b is greater than that of the first air permeable layer 310a.

Although the moist heating sheet 1 of the second embodiment has air permeability on the entire surface of both the side closer to the skin and the side farther from the skin, there are cases in which the sheet 1 is designed to have a non-air permeable region in part of its surface for the reason of, e.g., heat generation temperature control. For example, one side of the moist heating sheet 1 may be formed of an air permeable layer having a WVTR of x (g/$m^2 \cdot 24$ hr), and a sparingly moisture permeable sheet may be attached to an area of y (%) of the moisture permeable sheet to form a non-air permeable region. In that example, the WVTR of that side is x(100−y).

In the second embodiment, the first air permeable layer 310a is formed of the first moisture permeable sheet 33a and the nonwoven fabric 33d. Because the nonwoven fabric 33d has a sufficiently larger moisture permeability than the first moisture permeable sheet 33a, the moisture permeability of the first air permeable layer 310a is virtually equal to that of the moisture permeable sheet 33a. Likewise, the moisture permeability of the second air permeable layer 310b is virtually equal to that of the second moisture permeable sheet 33b.

Since the moist heating sheet 1 of the second embodiment lets air be fed to the heat generating part 2 mostly through the second air permeable layer 310b, heat generation proceeds from the peripheral to the central portions of the moist heating sheet 1 similarly to the moist heating sheet of the first embodiment. As a result, the moist heating sheet 1 is capable of generating steam stably for a prolonged period of time.

While the present invention has been described based on its preferred embodiments, the invention is not deemed to be limited to these embodiments. The details of the foregoing embodiments are interchangeable with each other.

EXAMPLES

The present invention will now be illustrated in greater detail with reference to the Examples, but it should be understood that the invention is not construed as being limited thereto. Unless otherwise noted, all the percents are by weight.

Example 1-1

A physiology enhancing device (moist heating sheet) of the embodiment illustrated in FIGS. 5 and 6 was prepared as follows.

(1) Preparation of Heat Generating Element of Sheet Form

A slurry (solids content: 0.3%) containing iron powder (RKH (trade name) from Dowa Iron Powder Co., Ltd.), activated carbon (Carboraffin (trade name) from Japan EnviroChemicals, Ltd.), and pulp fiber NBKP (Mackenzie (trade name) from Fletcher Challenge Canada, Ltd.) was formed into a sheet on an inclined short-wire paper machine at a line speed of 15 m/min to prepare a wet molded sheet. The molded sheet was dewatered between felt blankets, passed as such between 140° C. heated rolls to be dried. As a result of measurement with a thermogravimetric analyzer (TG/DTA 6200 from Seiko Instruments Inc.), the resulting molded sheet was found to be made up of 75% iron, 10% activated carbon, and 15% pulp. The weight of the sheet was 180 g/m².

The molded sheet obtained above was cut into 80 mm wide and 100 mm long sheets. Six cut sheets were stacked one on top of another, and 60 parts by weight of a 5% sodium chloride aqueous solution was syringed into the stack per 100 parts by weight of the stack to obtain a heat generating element of sheet form. The water retaining agent to water weight ratio was 0.44, and the oxidizable metal to reaction accelerator weight ratio was 7.5.

(2) Putting in Holder

A bag (holder) shown in FIGS. 5 and 6 was made using a moisture permeable film of calcium carbonate-containing polyethylene (WVTR: 800 to 1200 g/(m²·24 hr); air permeance: 10000±2000 s/100 cm³; thickness: 0.05 mm), a sparingly moisture permeable film of linear low density polyethylene, and air-through nonwoven fabric (thickness: 0.13 mm). The heat generating element of sheet form was put into the bag to obtain a moist heating sheet shown in FIGS. 5 and 6. The total thickness of the sheets on the steam release side was 0.18 mm, and the steam release area was 0.016 m².

Example 1-2

(1) Preparation of Heat Generating Element of Powder Form

A raw material composition was compounded from the following components.

| | |
|---|---|
| Oxidizable metal: iron powder (RKH (trade name) from Dowa Iron Powder Co., Ltd.) | 29.5% |
| Reaction accelerator: activated carbon (Carboraffin (trade name) from Japan EnviroChemicals, Ltd.) | 10% |
| Water retaining agent 1: acrylic acid-based superabsorbent polymer (Aquepearl, from Mitsubishi Chemical Corp.) | 7% |
| Water retaining agent 2: vermiculite (from NN Chemical Corp.) | 7% |
| Electrolyte: purified salt (NaCl) | 1.5% |
| Water: industrial water | 45% |

(2) Preparation of Moist Heating Device

The above components were uniformly compounded to prepare a heat generative mixed powder. A 20 g portion of the mixed powder was packed into the same holder as used in Example 1-1 to make a moist heating sheet shown in FIG. 5 and FIG. 6.

(3) Evaluation

To testify physiology enhancing effects of the resulting moist heating sheets, a clinical test on lower back pain reducing effects was carried out.

Figure 7A:
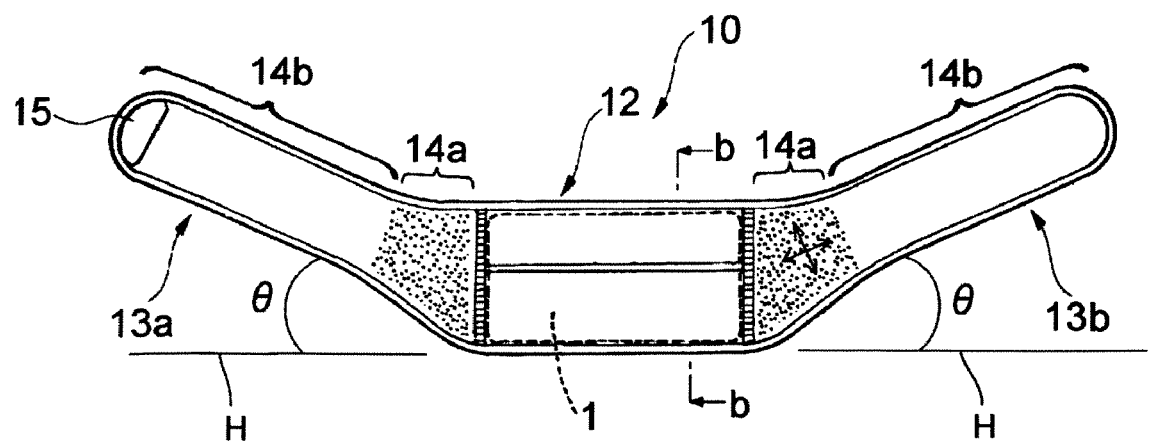
FIG. 7(a) is a plan of a holder containing the moist heating sheet shown in FIG. 3.
Figure 7B:
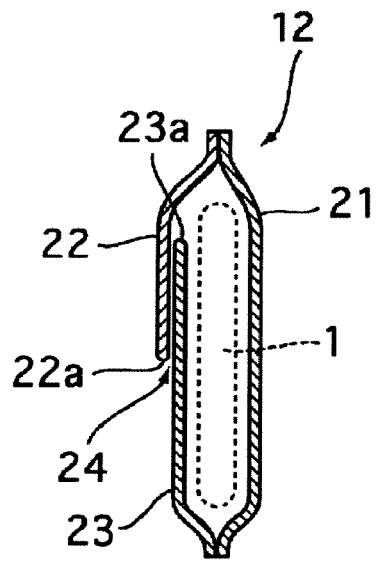
FIG. 7(b) is a cross-section taken along line b-b in FIG. 7(a).
Figure 13A:
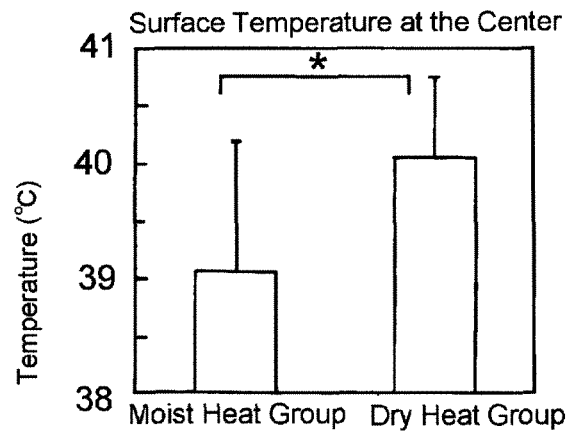
FIGS. 13(a), 13(b), and 13(c) are each a graph demonstrating the effect of a physiology enhancing device of the present invention in raising skin temperatures.
Figure 13B:
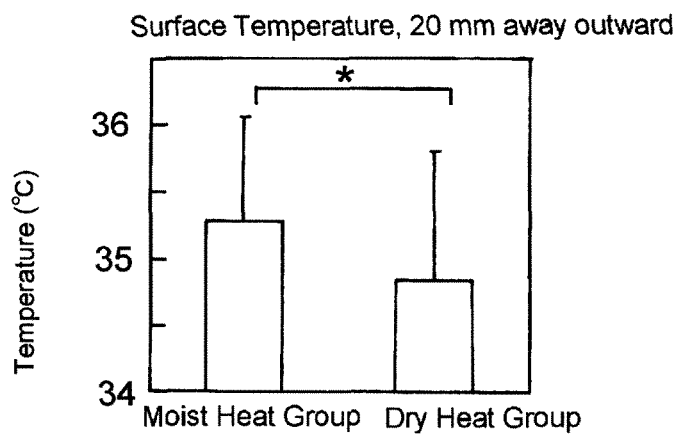
Figure 13C:
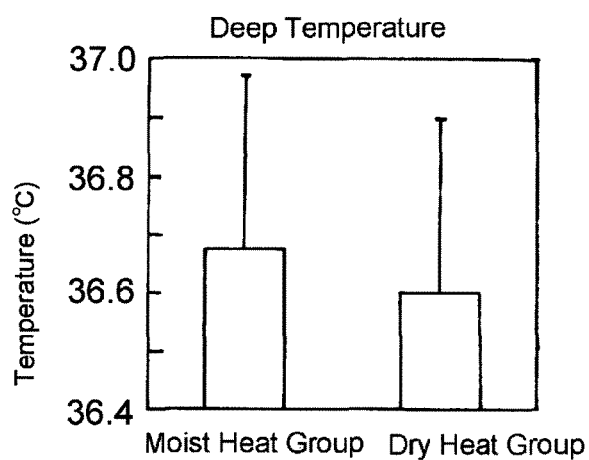

The moist heating sheet obtained in Example 1-1 was put into the holding part 12 of the attachment belt 10 shown in FIGS. 7(a) and 7(b) and applied to the lower back of each of eight test subjects. The first and second skin facing panels of the holding part 12 were formed of 0.26 mm thick knitted mesh fabric. The moist heating sheet was first applied with its steam release side facing the wearer's lower back (moist heat group). Next time, the opposite side of its steam release side was applied to face the wearer's lower back (dry heat group). Moist heat was applied to the lower back in the moist heat group. In the dry heat group, no steam but dry heat was applied to the lower back. The wearers' body temperatures were monitored during a period of from 60 minutes to 240 minutes from the start of application in a measuring environment of 20° C. and 40% RH and averaged. The measuring points were (a) the skin surface at the center of application site (surface temperature), (b) the skin surface 20 mm below the lower edge of the application site (surface temperature), and (c) 20 mm above the upper edge of the application site and 10 mm below the skin (deep temperature). The deep temperature was measured with a body thermometer Coretemp CM-210 equipped with a deep body temperature probe PD1, both from Terumo Corp. The results obtained are shown in FIGS. 13(a) through 13(c). In FIGS. 13(a) and 13(b), the mark * indicates that the probability P in the $x^2$ test is less than 0.05, showing that the difference is statistically significant.

Figure 14A:
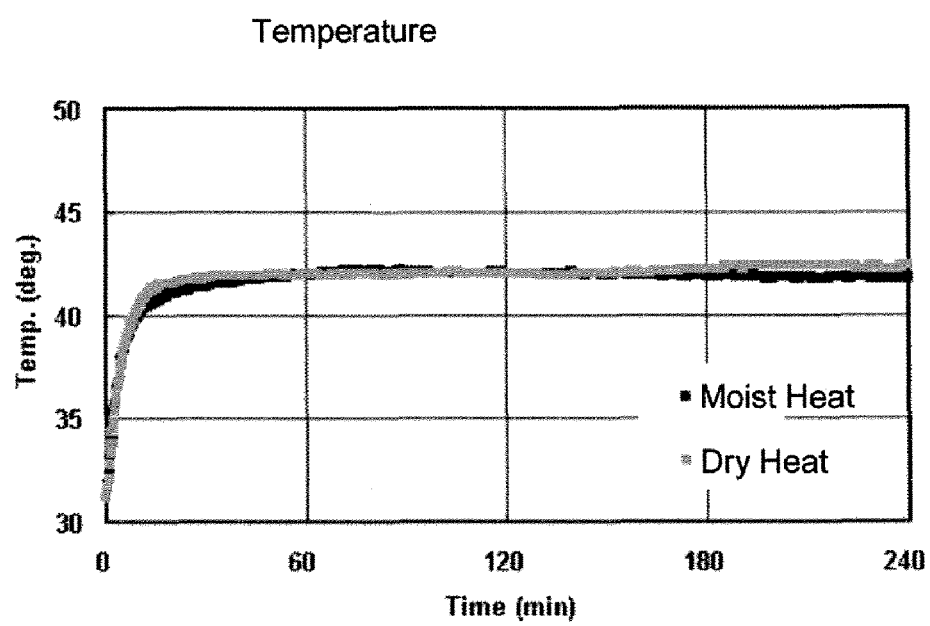
FIGS. 14(a) and 14(b) are graphs showing the results of measuring heat generation temperature and heat conductivity, respectively, of a physiology enhancing device according to the present invention.
Figure 14B:
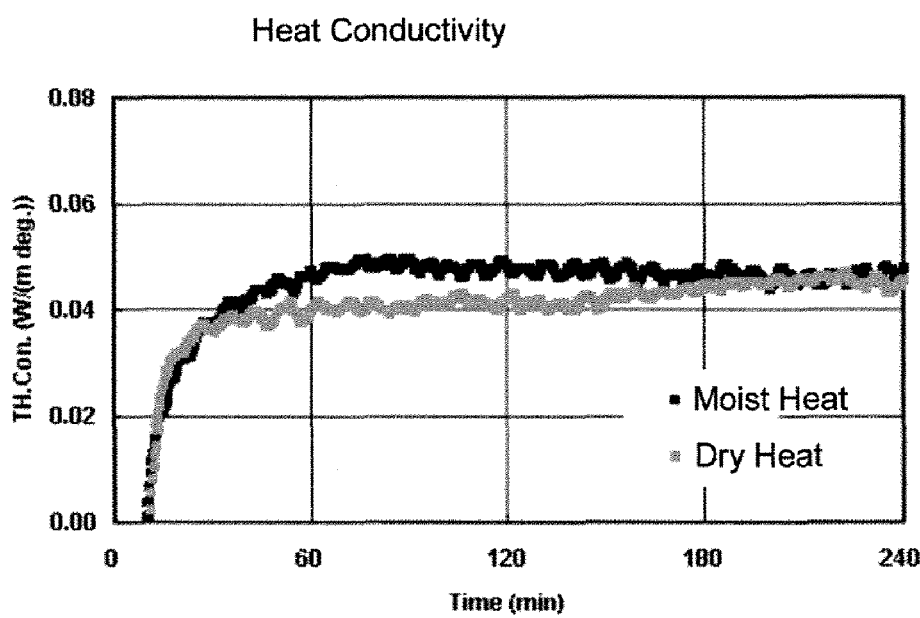

Separately, the thermal characteristics ((a) temperature and (b) heat conductivity) of the moist heating sheet were measured using the model measurement system illustrated in FIG. 3. The moist heating sheet obtained in Example 1-1 was placed with its steam release side facing the heat flux meter (for moist heat measurement) and opposite to the heat flux meter (for dry heat measurement). The results obtained are shown in FIGS. 14(a) and 14(b).

The results shown in FIGS. 13(a) to 13(c) apparently prove that the test subjects' skin temperatures rise higher when provided with heat accompanied by steam, namely moist heat, owing to the higher heat transfer efficiency of moist heat than with dry heat. The results shown in FIGS. 14(*a*) and 14(*b*) are especially noteworthy. These results verify that moist heat and dry heat have noticeably different heat conductivities even through their heat generation temperatures are equal, which indicates that moist heat achieves extremely higher heat transfer efficiency. While not shown in the drawing, the moist heating sheet obtained in Example 1-1 continued generating steam for a period of 4 hours and kept the body surface temperature at 39° C. The moist heating sheet obtained in Example 1-2 was evaluated in the same manner as described to give almost the same results as that of Example 1-1.

Additionally, the moist heating sheet obtained in Example 1-1 was placed on an acrylic resin plate with its steam release side down, and temperature rise characteristics from the contact with oxygen were measured in accordance with JIS S4100. The measurements were taken at (a) four points 1 cm inward from the four corners on the diagonals of the sheet, (b) four points 2 cm inward from the four corners on the diagonals of the sheet, and (c) three points near the intersection of the diagonals of the sheet. The results of the measurements are shown in FIGS. 15(*a*) through 15(*d*). The results apparently reveal that the temperature rise propagates with time from the peripheral to the central portions of the moist heating sheet. In other words, it is seen that heat generation proceeds from the peripheral to the central portions with time.

Example 2-1

The physiology enhancing device (moist heating sheet) illustrated in FIGS. 5 and 6 was prepared as follows.
(1) Preparation of Heat Generating Element of Sheet Form
   Formulation of raw material composition

| | |
|---|---|
| Fibrous material: pulp fiber NBKP (Mackenzie (trade name) from Fletcher Challenge Canada, Ltd.; CSF: 140 ml) | 8% |
| Oxidizable metal: iron powder (RKH (trade name) from Dowa Iron Powder Co., Ltd.) | 84% |
| Reaction accelerator: activated carbon (Carboraffin (trade name) from Japan EnviroChemicals, Ltd.) | 8% |

To the composition of the above components were added 0.7 parts by weight of a polyamide-epichlorohydrin resin (WS4020 (trade name) from Seiko PMC Corp.) as a cationic flocculent and 0.18 parts by weight of sodium carboxymethyl cellulose (HE1500f (trade name) from Dai-ichi Kogyo Seiyaku Co., Ltd.) as an anionic flocculent per 100 parts by weight of the solids content of the raw material composition (i.e., the total of the fibrous material, the oxidizable metal, and the reaction accelerator). Water (industrial water) was added thereto to result in a solids concentration of 12% to prepare a slurry.
(2) Papermaking Conditions
The slurry was diluted with water to a concentration of 0.3% immediately before the head box and formed into a sheet on an inclined short-wire paper machine at a line speed of 15 n/min to prepare a wet molded sheet.
(3) Drying Conditions
The wet molded sheet was dewatered between felt blankets, passed as such between 140° C. heated rolls to be dried to a water content of 5% or less to obtain a molded sheet having a grammage of 450 g/m$^2$ and a thickness of 0.45 mm.

As a result of measurement with a thermogravimetric analyzer (TG/DTA 6200 from Seiko Instruments Inc.), the resulting molded sheet was found to be made up of 84% iron, 8% activated carbon, and 8% pulp.
(4) Preparation of Heat Generating Sheet
The molded sheet was cut into 80 mm wide and 100 mm long sheets. Two cut sheets were stacked on each other, and 50 parts by weight of an electrolytic solution described below was syringed into the stack per 100 parts by weight of the stack and penetrated throughout the two thicknesses by capillarity to obtain a heat generating sheet (heat generating element of sheet form).
Electrolytic Solution:
   Electrolyte: purified salt (NaCl)
   Water: industrial water
   Concentration: 5%
(5) Putting in Holder
A bag (holder) shown in FIGS. 5 and 6 was made using a moisture permeable film of calcium carbonate-containing polyethylene (WVTR: 800 to 1200 g/m$^2$·24 hr; air permeance: 10000±2000 s/100 cm$^3$), a sparingly moisture permeable sheet of linear low density polyethylene, and air-through nonwoven fabric. The two-ply heat generating sheet was put into the bag to obtain a moist heating sheet shown in FIGS. 5 and 6. The steam release area was 0.016 m$^2$.

Comparative Example 2-1

Two thicknesses of a moisture permeable film of calcium carbonate-containing is polyethylene (WVTR: 800 to 1200 g/m$^2$·24 hr; air permeance: 10000±2000 s/100 cm$^3$), a sparingly moisture permeable sheet of linear low density polyethylene, and air-through nonwoven fabric were stacked one on top of another, and joined at the four side edges of the stack to make a bag. The same two-ply heat generating sheet obtained in Example 2-1 was packed in the bag to obtain a heat generating sheet of dry heat type.

The moist heating sheet obtained in Example 2-1 was applied to the left lower back of a 30-year-old male test subject for 5 hours. The heat generating sheet of dry heat type obtained in Comparative Example 2-1 was applied to the right lower back of the same test subject for 5 hours. The moist heating sheet of Example 2-1 was attached with its moisture permeable film side facing the skin, and the dry heat type heat generating sheet of Comparative Example 2-1 was attached with its sparingly moisture permeable film/air-through nonwoven fabric side facing the skin. The environmental temperature was 20±1° C. The water content of the horny layer under the sheet, the humidity between the sheet and the skin, and the skin surface temperature under the sheet were monitored during the application in accordance with the following methods.

As a result, the moist heating sheet of Example 2-1 showed the following results. The humidity between the sheet and the skin reached 80% RH in about 15 to 20 minutes and maintained that level for 5 hours. The horny layer's water content, which was about 0.16 to 0.17 g/cm$^3$ before the application, exceeded 0.25 g/cm$^3$ in 30 minutes and thereafter hovered at between 0.26 and 0.32 g/cm$^3$ to the end of the 5 hour application. The skin surface temperature of the application site hovered at between 38° C. and 39° C. after 30 minutes to 5 hours from the start of application.

The dry heat type heat generating sheet of Comparative Example 2-1 showed the following results. The humidity between the sheet and the skin reached 40% RH in about 15 to 20 minutes and maintained that level for 5 hours. The horny layer's water content, which was about 0.16 to 0.17 g/cm$^3$ before the application, reached about 0.20 g/cm³ in 10 minutes and thereafter hovered at between 0.20 and 0.24 g/cm³ to the end of the 5 hour application. The skin surface temperature of the application site hovered at between 38° C. and 39° C. after 30 minutes to 5 hours from the start of application, which was practically equal to the corresponding results of Example 2-1.

Figure 16:
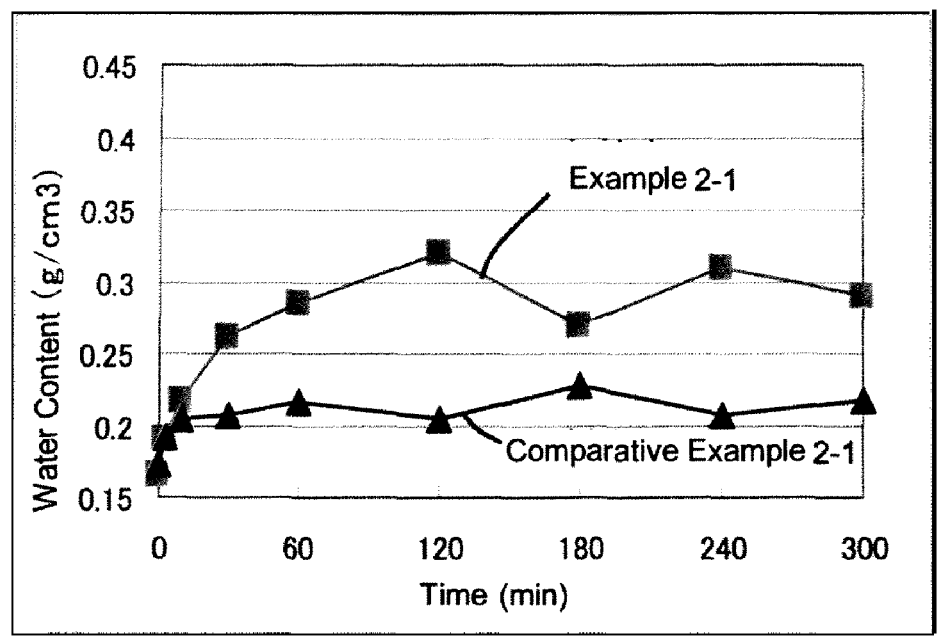
FIG. 16 is a graph of horny layer's water contents in Example 2-1 and Comparative Example 2-1.
Figure 17:
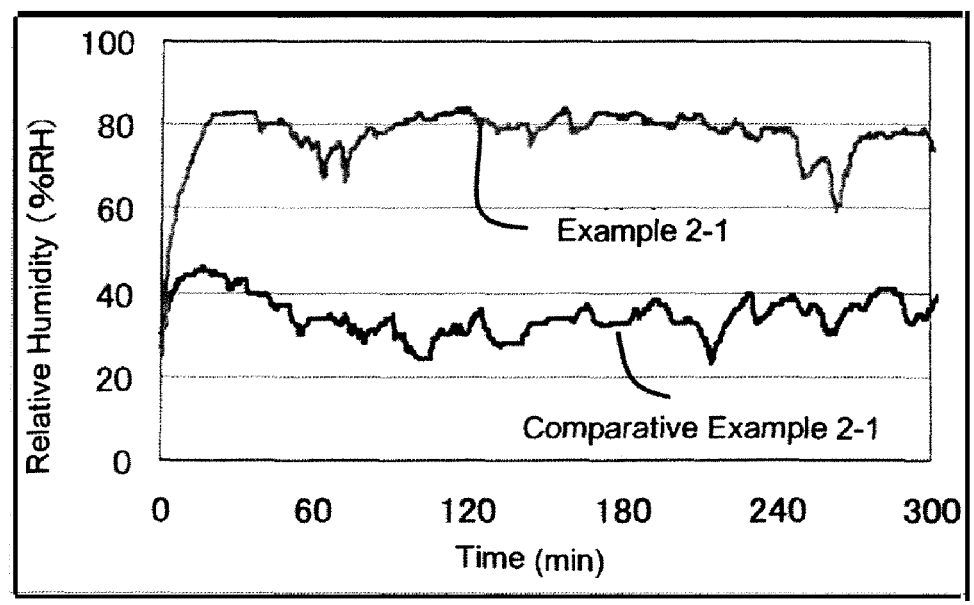
FIG. 17 is a graph showing humidities in Example 2-1 and Comparative Example 2-1.
Figure 18:
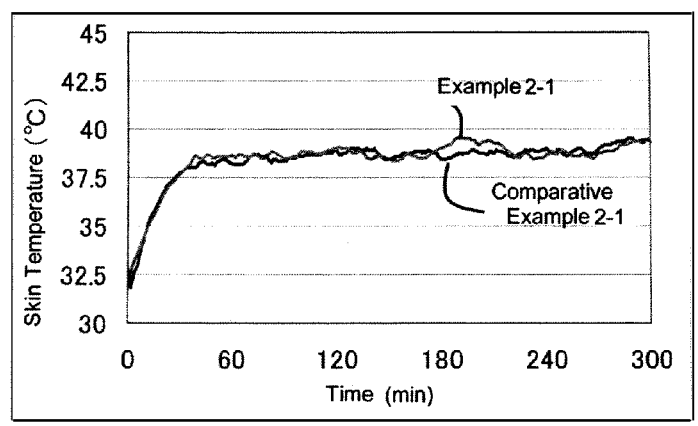
FIG. 18 is a graph showing skin surface temperatures in Example 2-1 and Comparative Example 2-1.

The results of the above measurements are graphically shown in FIGS. 16 to 18.

Measurement of Horny Layer's Water Content

The water content of the horny layer (about 20 μm deep) was measured by TDR. The method of TDR is reported by S. Naito and M. Hoshi in *Review of Scientific* Instruments, Vol. 67, No. 10, 1996, pp. 3633-3641, "A method of measuring surface permittivity by microwave dielectric analysis". The measuring environment was 20° C. and 40% RH. Twenty minutes before each measuring time (5, 10, 30, 60, 120, 180, 240, and 300 minutes after the application), a test subject entered a chamber so conditioned. The operations for measuring the water content of the horny layer, including stripping the test sheet off the skin and applying the probe to the skin, were carried out quickly. The measuring points were 10 mm away upward from and 10 mm away downward from the center of the sheet. The measurement was taken 7 times for each point to give 14 measurements in total, which were averaged to yield the water content of the horny layer. The sheet was re-applied to the skin immediately after taking each measurement.

Measurement of Humidity Between Sheet and Skin

A humidity sensor (Thermo Recorder TR-72U equipped with a temperature/humidity sensor, from T& D Corp.) was fixed with an adhesive tape to the skin at the center of the application site. After that, the sheet was applied thereon, and the humidity was monitored for 5 hours.

Measurement of Skin Surface Temperature

A temperature sensor (handy type temperature data logger LT-8 equipped with a skin temperature sensor LT-ST08-12, from Gram Corp.) was fixed with an adhesive tape to the skin at the center of the application site. After that, the sheet was applied thereon, and the temperature was monitored for 5 hours.

Comparative Example 2-2

Figure 19A:
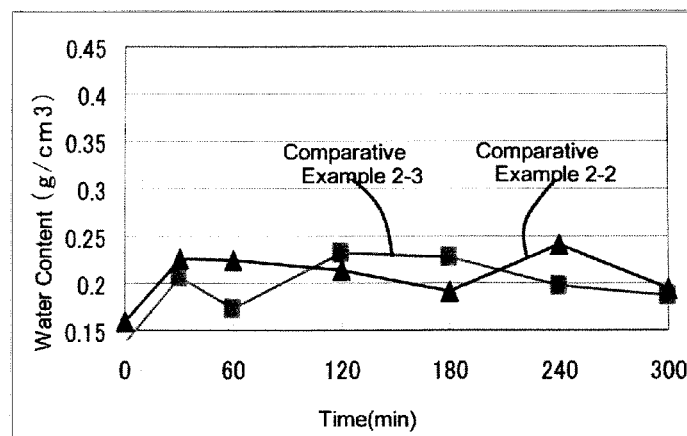
FIGS. 19(a) and 19(b) are graphs showing horny layer's water content and skin surface temperature, respectively, in Comparative Examples 2-2 and 2-3.
Figure 19B:
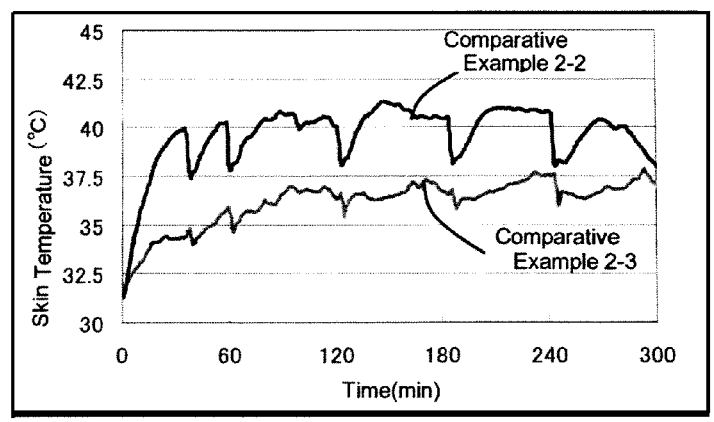

Salonship Hot (trade name) available from Hisamitsu Pharmaceutical Co., Inc. was applied to the left lower back of a test subject for 5 hours in an environment at 20±1° C. The water content of the subject's horny layer, which was about 0.16 to 0.17 g/cm³ before the application, rose to about 0.23 g/cm³ in 30 minutes and hovered at between 0.20 and 0.25 g/cm³ thereafter to the end of the 5 hour application. The skin surface temperature in the application site was between 40° C. and 42° C. from after 30 minutes to 5 hours from the application. The changes in horny layer water content and skin surface temperature are graphically shown in FIGS. 19(a) and 19(b).

Comparative Example 2-3

Salonship Hot (trade name) available from Hisamitsu Pharmaceutical Co., Inc. was applied inside out (i.e., with the side that is not to face the skin in normal usage facing the skin) to the left lower back of a test subject for 5 hours. The environmental temperature was 20±1° C. The water content of the subject's horny layer, which was about 0.16 to 0.17 g/cm³ before the application, rose to about 0.20 g/cm³ in 30 minutes and hovered at between 0.16 and 0.24 g/cm³ thereafter to the end of the 5 hour application. The skin surface temperature in the application site was between 34° C. and 38° C. from after 30 minutes to 5 hours from the application. The changes in horny layer water content and skin surface temperature are graphically shown in FIGS. 19(a) and 19(b).

Comparative Example 2-4

Figure 20A:
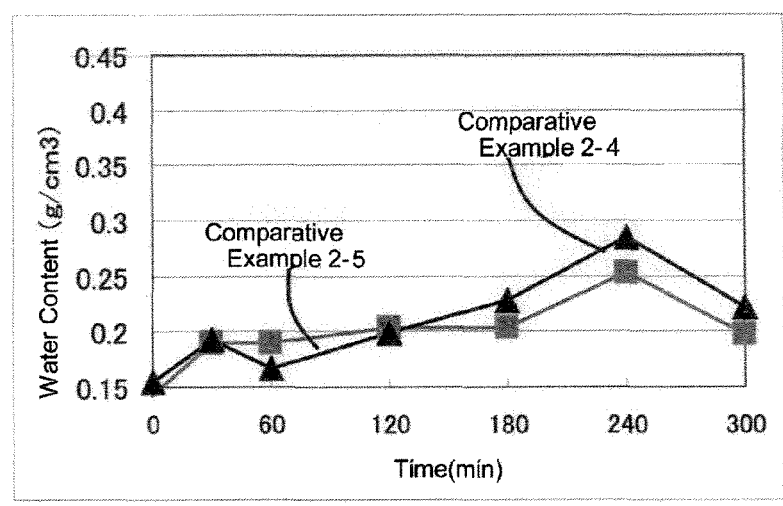
FIG. 20(a) and FIG. 20(b) are graphs showing horny layer's water content and skin surface temperature, respectively, in Comparative Examples 2-4 and 2-5.
Figure 20B:
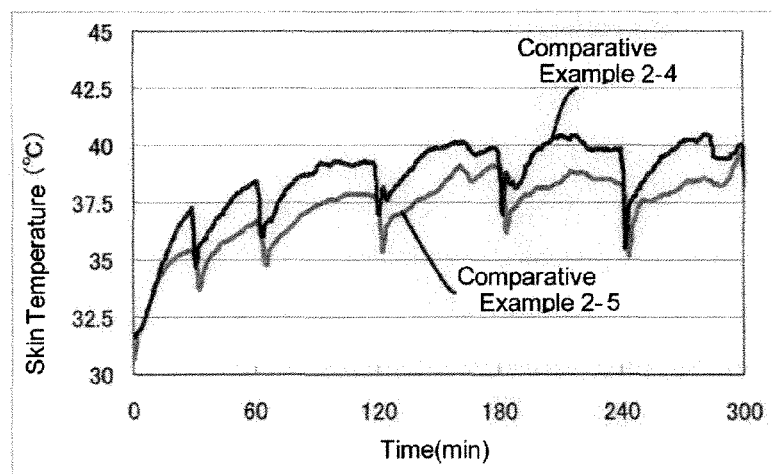

Thermacare Therapeutic Heat Back Wraps (trade name) available from Procter & Gamble was applied to the left lower back of a test subject for 5 hours in an environment at 20±1° C. The water content of the subject's horny layer, which was about 0.15 to 0.16 g/cm³ before the application, rose to about 0.19 g/cm³ in 30 minutes and hovered at between 0.16 and 0.29 g/cm³ thereafter to the end of the 5 hour application. The skin surface temperature in the application site was between 37° C. and 41° C. from after 30 minutes to 5 hours from the application. The changes in horny layer water content and skin surface temperature are graphically shown in FIGS. 20(a) and 20(b).

Comparative Example 2-5

Thermacare Therapeutic Heat Back Wraps (trade name) available from Procter & Gamble was applied inside out (i.e., with the side that is to face outside in normal usage facing the skin) to the left lower back of a test subject for 5 hours in an environment at 20±1° C. The water content of the subject's horny layer, which was about 0.14 to 0.15 g/cm³ before the application, rose to about 0.19 g/cm³ in 30 minutes and hovered at between 0.19 and 0.26 g/cm³ thereafter to the end of the 5 hour application. The skin surface temperature in the application site was between 35° C. and 40° C. from after 30 minutes to 5 hours from the application. The changes in horny layer water content and skin surface temperature are graphically shown in FIGS. 20(a) and 20(b).

Example 3-1

(1) Preparation of Heat Generating Element of Powder Form

Iron powder (RKH (trade name) from Dowa Iron Powder Co., Ltd.), a superabsorbent polymer, and vermiculite were mixed uniformly. A 4.5% sodium chloride aqueous solution was mixed therein uniformly. Activated carbon (Carboraffin (trade name) from Japan EnviroChemicals, Ltd.) was then mixed therein uniformly to obtain a heat generating element of powder form, the composition of which is shown below. The water retaining agent to water weight ratio was 0.44, and the oxidizable metal to reaction accelerator weight ratio was 20.

| | |
|---|---|
| Iron powder | 41% |
| Superabsorbent polymer | 10% |
| Vermiculite | 7% |
| Activated carbon | 2% |
| Sodium chloride | 1.8% |
| Water | 38.2% |

(2) Preparation of Moist Heating Device

A bag (holder) shown in FIGS. 5 and 6 was made using a moisture permeable film of calcium carbonate-containing polyethylene (WVTR: 800 to 1200 g/(m²·24 hr); air permeance: 10000±2000 s/100 cm³; thickness: 0.05 mm), a sparingly moisture permeable film of linear low density polyethylene, and air-through nonwoven fabric (thickness: 0.13 mm). The heat generating element of powder form was put into the bag to obtain a moist heating device shown in FIGS. 5 and 6. The total thickness of the sheets on the steam release side was 0.18 mm.

(3) Control

A dry heat type body warmer that generated little steam was prepared as a control of the moist heating device of Example 3-1. The body warmer was designed to have the same heat generation temperature as the device of Example 3-1. Specifically, the components below were mixed up to obtain a heat generating element. The water retaining agent to water weight ratio was 1.75, and the oxidizable metal to reaction accelerator weight ratio was 5.

| | |
|---|---|
| Iron powder | 55% |
| Superabsorbent polymer | 1% |
| Vermiculite | 20% |
| Activated carbon | 11% |
| Sodium chloride | 1% |
| Water | 12% |

A bag (holder) shown in FIGS. 5 and 6 was made using a moisture permeable film of calcium carbonate-containing polyethylene (WVTR: 1000 g/(m$^2$·24 hr); air permeance: 10000 s/100 cm$^3$), a sparingly moisture permeable film of linear low density polyethylene, and air-through nonwoven fabric. The heat generating element of powder foam was put into the bag to obtain disposable heat body pack body warmers of dry heat as illustrated in FIGS. 5 and 6.

(4) Evaluation

The heat generating element of the resulting moist heating device was evaluated by measuring the rate of steam generation (amount of steam released per unit time) and the cumulative amount of steam released in 30 minutes from the start of heat generation in accordance with the previously described methods. In Example 3-1, the results were: (1) The rate of steam generation reached the maximum after 3.5 minutes from the start of heat generation. (2) The maximum rate of steam generation was 0.055 g/min per gram of iron powder. (3) The cumulative amount of steam released was 0.2 g per gram of the heat generating element. The moist heating device continued generating steam over a 5 hour period, during which time the body surface temperature was maintained at 39° C. Furthermore, the effect of the moist heating device in giving a feeling of relaxation was testified using the dry heat type body warmer as a control as follows. The moist heating device was put in the attachment belt 10 illustrated in FIGS. 8(*a*) and 8(*b*) and attached to the abdomen of each test subject in the fashion illustrated. The moist heating device was attached with its steam release side facing the abdomen. The dry heat type body warmer was applied in the same way. The thickness of the sheet of the attachment belt 10 which held the moist heating device was 0.8 mm. The subject pool consisted of five female adults suffering from oversensitivity to cold. Evaluations were made in terms of the following items (A) to (C), which, as previously stated, are widely recognized in physiological sciences as measures for judging which of parasympathetic and sympathetic nervous systems is dominant. In every evaluation test, the test subjects were habituated for 30 minutes prior to attachment of the moist heating device or dry heat type body warmer. Each of the moist heating device and dry heat type body warmer was applied for 60 minutes and then detached. The values in Table 1 below are relative percentages to the values of habituated test subjects. The values in Table 1 are expressed in terms of average±standard error.

(A) Pupil Diameter D1 Before Light Stimulation, Pupil Diameter Change D2 Due to Light Stimulation, and Pupillary Contraction Rate CR A smaller pupil diameter D1 (mm) before light stimulation indicates higher dominance of the parasympathetic nervous system. A greater pupil diameter change D2 due to light stimulation indicates higher dominance of the parasympathetic nervous system. The higher the pupillary contraction rate CR, which is calculated from D2/D1, the higher the dominance of the parasympathetic nervous system.

(B) Electrocardiographic (ECG) R-R Interval Variability Analysis

Frequency analysis of the peak-to-peak time interval between ventricular contractions was performed to determine LF and HF values. An HF component is an index of parasympathetic activity. A greater HF component is a sign of higher dominance of the parasympathetic nervous system. An LF/HF ratio is an index of sympathetic activity. A larger LF/HF ratio indicates higher dominance of the sympathetic nervous system.

(C) Total Hemoglobin Content

The total hemoglobin content at a finger tip was measured by near infrared spectroscopy at two wavelengths (780 nm and 830 n). A finger tip is a region under high sympathetic dominance. An increased total hemoglobin content is a sign of decreased sympathetic dominance.

TABLE 1

| | 20 mins after Attachment | 40 mins after Attachment | 60 mins after Attachment | 15 mins after Detachment | 30 mins after Detachment |
|---|---|---|---|---|---|
| | Pupil Diameter D1 before Light Stimulation | | | | |
| Moist Heat | 97.56 ± 0.522 | 89.96 ± 2.534 | 94.82 ± 1.525 | 93.16** ± 1.525 | 91.84** ± 2.019 |
| Dry Heat | 96.64 ± 1.076 | 92.44 ± 1.856 | 98.56 ± 0.632 | 103.1** ± 0.173 | 105.92** ± 0.924 |
| | Pupil Diameter Change D2 due to Light Stimulation | | | | |
| Moist Heat | 107.66 ± 4.827 | 131.18 ± 8.778 | 114.66 ± 3.901 | 116.12 ± 4.761 | 121.52** ± 6.061 |
| Dry Heat | 122.9 ± 4.509 | 142.26 ± 17.827 | 107.9 ± 4.722 | 85.58 ± 4.975 | 77.66** ± 6.577 |
| | Pupillary Contraction Ratio CR | | | | |
| Moist Heat | 110.3 ± 4.36 | 145.44 ± 7.07 | 121.12 ± 4.60 | 124.74* ± 5.24 | 132.48** ± 6.32 |
| Dry Heat | 127.2 ± 4.54 | 154.86 ± 21.34 | 109.46 ± 4.73 | 83.1* ± 5.26 | 73.52** ± 6.65 |
| | ECG R-R Interval Analytical Results: HF | | | | |
| Moist Heat | 105.22 ± 4.34 | 239.26 ± 61.28 | 112.66 ± 5.27 | 151.63 ± 8.03 | 162.92 ± 14.19 |
| Dry Heat | 116.47 ± 12.59 | 175.09 ± 46.11 | 136.26 ± 22.70 | 85.26 ± 5.33 | 74.2 ± 9.78 |

TABLE 1-continued

|  | 20 mins after Attachment | 40 mins after Attachment | 60 mins after Attachment | 15 mins after Detachment | 30 mins after Detachment |
|---|---|---|---|---|---|
| | | | LF/HF | | |
| Moist Heat | 75.65 ± 10.19 | 29.48 ± 6.23 | 52.28* ± 6.27 | 50.18 ± 4.85 | 42.7 ± 4.61 |
| Dry Heat | 119.07 ± 12.30 | 127.93 ± 20.55 | 556.98* ± 225.57 | 209.25 ± 56.51 | 422.39 ± 165.10 |
| | | | Total Hemoglobin Content | | |
| Moist Heat | 227.5 ± 29.46 | 256.94 ± 35.24 | 297.78* ± 39.93 | 323.9** ± 47.40 | 343.62** ± 51.67 |
| Dry Heat | 109.16 ± 6.50 | 121.84 ± 12.49 | 124.34* ± 16.17 | 127.66** ± 13.30 | 136.34** ± 20.15 |

*Probability in the $x^2$ test <0.05
**Probability in the $x^2$ test <0.01

As is apparent from the results in Table 1, the moist heating device of Example 3-1 that generates moist heat brings about parasympathetic dominance as compared with the dry heat type body warmer in terms of all the evaluation items. What is noteworthy is that the parasympathetic dominance outlasts the application period. This is considered because the deep body temperature is raised by moist heat so that the promotion of blood circulation outlasts the application of the device.

Example 3-2

(1) Preparation of Heat Generating Element of Sheet Form

A slurry (solids content: 0.3%) containing iron powder (RKH (trade name) from Dowa Iron Powder Co., Ltd.), activated carbon (Carboraffin (trade name) from Japan Enviro-Chemicals, Ltd.), and pulp fiber NBKP (Mackenzie (trade name) from Fletcher Challenge Canada, Ltd.) was formed into a sheet on an inclined short-wire paper machine at a line speed of 15 m/min to prepare a wet molded sheet. The molded sheet was dewatered between felt blankets, passed as such between 140° C. heated rolls to be dried. As a result of measurement with a thermogravimetric analyzer (TG/DTA 6200 from Seiko Instruments Inc.), the resulting molded sheet was found to be made up of 75% iron powder, 10% activated carbon, and 15% pulp. The weight of the sheet was 180 g/m².

The molded sheet was cut into 80 mm wide and 100 mm long sheets. Six cut sheets were stacked one on top of another, and 60 parts by weight of a 5% sodium chloride aqueous solution was syringed into the stack per 100 parts by weight of the stack to obtain a heat generating element of sheet form. The water retaining agent to water weight ratio was 0.44, and the oxidizable metal to reaction accelerator weight ratio was 7.5.

(2) Making of Moist Heating Device

The heat generating element of sheet form was put into the same holder as used in Example 3-1 to obtain a moist heating device illustrated in FIGS. 5 and 6.

(3) Control

The same control as used in Example 3-1 was used.

(4) Evaluation

Evaluations were made in the same manner as in Example 3-1. The results were: (1) The rate of steam generation reaches the maximum after 10 to 12 minutes from the start of heat generation. (2) The maximum rate of steam generation was 0.052 g/min per gram of iron powder. (3) The cumulative amount of steam released in 30 minutes from the start of heat generation was 0.1 to 0.4 g per gram of the heat generating sheet. The moist heating device continued generating steam over a 5 hour period, during which time the body surface temperature was maintained at 39° C. The following evaluation item (D) was added to items (A) to (C). The subject pool consisted of five healthy male adults.

(D) Electrogastrography

Gastric motility (3 cpm (3 cycles per minute)) and intestinal motility (6 cpm (6 cycles per minute)) were measured. The higher the value, the higher the parasympathetic dominance.

TABLE 2

|  | 20 mins after Attachment | 40 mins after Attachment | 60 mins after Attachment | 15 mins after Detachment | 30 mins after Detachment |
|---|---|---|---|---|---|
| | | Pupil Diameter D1 before Light Stimulation | | | |
| Moist Heat | 88.9 | 94.4 | 91 | 90 | 94.5 |
| Dry Heat | 110.3 | 112.5 | 105.1 | 122.2 | 115.8 |
| | | Pupil Diameter Change D2 due to Light Stimulation | | | |
| Moist Heat | 122.3 | 133.3 | 142.3 | 142 | 143.2 |
| Dry Heat | 92.2 | 91.2 | 106.2 | 100 | 110.9 |
| | | Pupillary Contraction Ratio CR | | | |
| Moist Heat | 140 | 140.4 | 157.3 | 157.5 | 153.3 |
| Dry Heat | 82.7 | 82.6 | 101.8 | 90.4 | 97.2 |
| | | ECG R-R Interval Analytical Results: HF | | | |
| Moist Heat | 137.8 | 128.4 | 197.9 | | |
| Dry Heat | 96.3 | 122.2 | 77.8 | | |
| | | LF/HF | | | |
| Moist Heat | 104.2 | 76.6 | 67.2 | | |
| Dry Heat | 134.6 | 181.2 | 155.9 | | |

TABLE 2-continued

|  | 20 mins after Attachment | 40 mins after Attachment | 60 mins after Attachment | 15 mins after Detachment | 30 mins after Detachment |
|---|---|---|---|---|---|
| Total Hemoglobin Content ||||||
| Moist Heat | 101.6 | 99.7 | 95.7 | | |
| Dry Heat | 99.6 | 98.5 | 95.5 | | |
| Electrogastrography: 3 cpm (stomach) ||||||
| Moist Heat | 200 | 210.5 | 152.6 | | |
| Dry Heat | 121.3 | 37.9 | 63.5 | | |
| 6 cpm (intestines) ||||||
| Moist Heat | 195.5 | 163.6 | 122.7 | | |
| Dry Heat | 182.1 | 13.6 | 10 | | |

As is apparent from the results in Table 2, the moist heating device of Example 3-2 that generates moist heat brings about parasympathetic dominance as compared with the dry heat type body warmer in terms of all the evaluation items similarly to the device of Example 3-1. It is also seen that the parasympathetic dominance outlasts the application period.

Example 4-1

A moist heating device (moist heating sheet) illustrated in FIGS. 5 and 6 was made in the same manner as in Example 2-1.

Evaluation-1

Figure 8A:
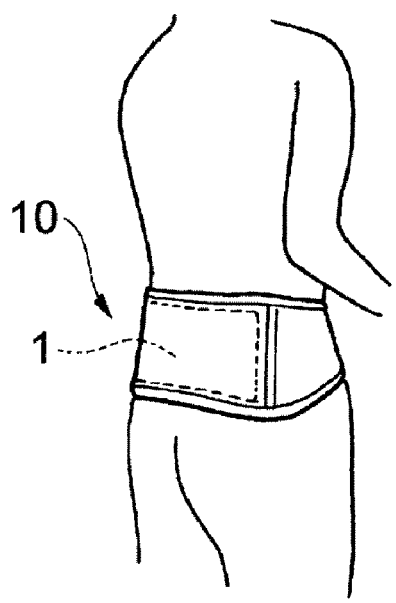
FIG. 8(a) illustrates the moist heating sheet of FIG. 3 applied to the lower back, and FIG. 8(b) to the abdomen.

To demonstrate physiology enhancing effects of the resulting moist heating sheet, a clinical test on lower back pain reducing effects was carried out. The moist heating sheet was put into the holding part 12 of the attachment belt 10 shown in FIGS. 7(a) and 7(b) and applied to the lower back of each test subject as illustrated in FIG. 8(a). The test subjects were divided into a group in which the moist heating sheet was applied with its steam release side facing the wearer's lower back (moist heat group) and a group in which the opposite side of its steam release side faced the wearer's lower back (dry heat group). In the moist heat group, moist heat was applied to the lower back. In the dry heat group, no steam but dry heat was applied. The moist heat group consisted of 28 test subjects, and the dry heat group 27. The test subjects were males and females aged 23 to 67 who had been aware of lower back pain or lower back and leg pain for the last six or more months. The symptoms of the subjects of the two groups before the testing were as shown in Table 3 below. The subjects wore the moist heating sheet 8 hours a day for consecutive 4 weeks and rated their back pain after detaching the moist heating sheet everyday in accordance with the scoring system: 1=no pain; 2=occasional slight pain; 3=constant pain sometimes with strong pain; 4=constant severe pain.

Figure 21A:
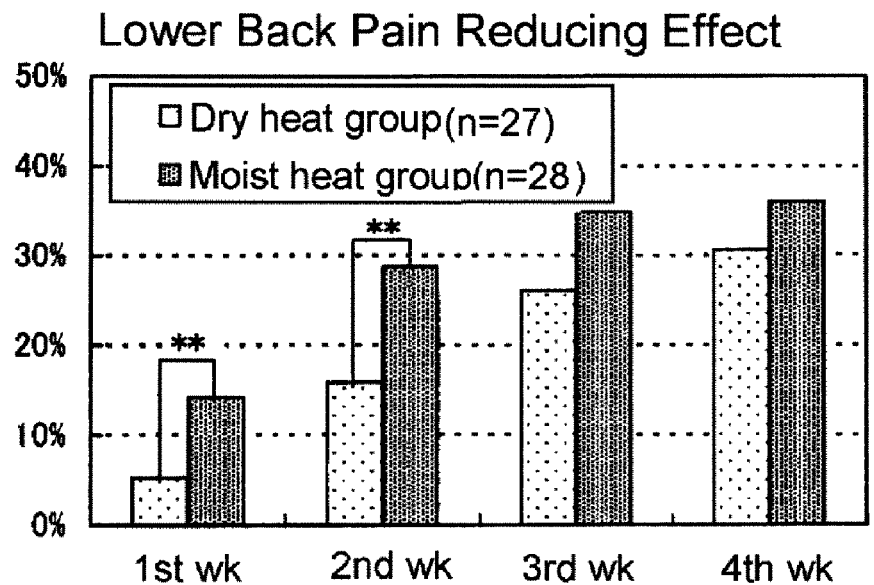
FIG. 21(a) and FIG. 21(b) are each a graph showing the lower back pain relief effect by a moist heating device according to the present invention.
Figure 21B:
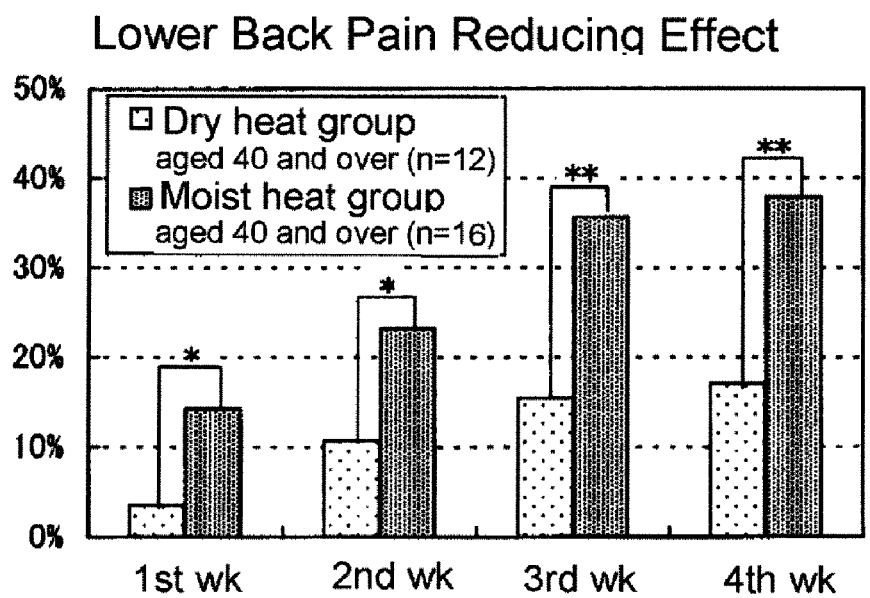

The scores were added up and averaged every week for each group. The percentage of the subjects who rated 1 was taken as a cure rate, provided that those who rated the pain as 1 immediately before the start of the testing were counted out. The change in cure rate was compared between the moist heat group and the dry heat group every week. The results are graphically shown in FIGS. 21(a) and 22(b). FIG. 21(a) shows the results of all the test subjects, and FIG. 21(b) the results of those aged 40 and over. In FIGS. 21(a) and 21(b), the mark * indicates that the probability P in the $x^2$ test is less than 0.03, and the mark ** indicates that the probability P in the same test is less than 0.01. Both indicate that the difference is statistically significant.

Separately, various characteristics of the moist heating sheet were measured by the above methods while worn by the subjects of the moist heat group. The results obtained are shown in Table 4.

As is apparent from the results in FIGS. 21(a) and 21(b), the lower back pain is is reduced more in the moist heat group than in the dry heat group. In particular, it is seen that the lower back pain reducing effect is significantly pronounced on the subjects aged 40 years and over, the middle and older generations suffering from lower back pain.

TABLE 3

|  | Moist Heat Group | Dry Heat Group |
|---|---|---|
| No pain | 0% | 0% |
| Occasional slight pain | 50% | 50% |
| Constant pain | 42% | 40% |
| Constant severe pain | 8% | 10% |

TABLE 4

| Duration of Skin Surface Temp. of 38-49° C. | Cumulative Amount of Steam Released | Highest Temp. Reached |
|---|---|---|
| 6.5 hr | 6.3 (mg/3 hr · cm$^2$) | 48° C. |

Evaluation-2

A clinical test different from evaluation-1 was conducted to examine lower back pain reducing effects. The test group was only a moist heat group consisting of 30 females aged 45 to 64 who suffered from chronic lower back pain. The test subjects wore the moist heating sheet 8 hours a day for consecutive 2 weeks and rated their lower back pain with respect to each of the three symptoms, (1) pain, (2) heavy feeling, and (3) listless feeling, after detaching the moist heating sheet everyday. The scoring system was: 0=no symptom; 1=not so worried; 2=slightly worried; 3=worried; 4=very worried.

After the 2 week wearing, the scores of all the subjects were added up and averaged for each symptom, and the average score was compared with that before the testing. Furthermore, all the scores were added up and averaged to provide an overall evaluation. The results are graphically represented in FIGS. 22(a) through 22(d).

As is apparent from the results shown in FIGS. 22(a) to 22(d), applying the moist heating sheet to the lower back for two weeks proved obviously effective in reducing lower back pain.

Evaluation-3

Positive effects on abdominal symptoms were clinically tested. The test group was a moist heat group consisting of 25 females aged 45 to 64 who had abdominal symptoms. The test subjects wore the moist heating sheet in a fashion illustrated in FIG. 8(b) 8 hours a day for consecutive 2 weeks and rated their abdominal conditions in terms of the following symptoms: (1) constipation, (2) diarrhea-like symptoms, (3) bloating sensation, and (4) pain, after detaching the moist heating sheet everyday. The scoring system was: 0=no symptom; 1=not so worried; 2=slightly worried; 3=worried; 4=very worried.

After the two week test, the scores of all the subjects were added up and averaged for each symptom, and the average score was compared with that before the testing. The results are graphically shown in FIGS. 23(a) through 23(d).

As is apparent from the results in FIGS. 23(a) to 23(d), applying the moist heating sheet to the abdomen for 2 weeks proves to produce obviously positive effects on the abdominal symptoms.

Evaluation-4

Positive effects on constipation symptom were clinically tested. The test group was a moist heat group consisting of 26 females aged 45 to 64 who had abdominal symptoms, suffering constipation (those who had abdominal symptoms scored 4 or 5 according to the scoring system below). The test subjects wore the moist heating sheet in a fashion illustrated in FIG. 8(b) 8 hours a day for consecutive 3 weeks. The test subjects recorded their daily bowel movement for one week before the test and during the testing period. The records are summarized in FIG. 24, in which the total number of days with a bowel movement per week is shown, the week before the test being taken as 0 week. The constipation scoring system was: 1=no symptom; 2=not so worried; 3=slightly worried; 4=worried; 5=very worried.

Figure 24:
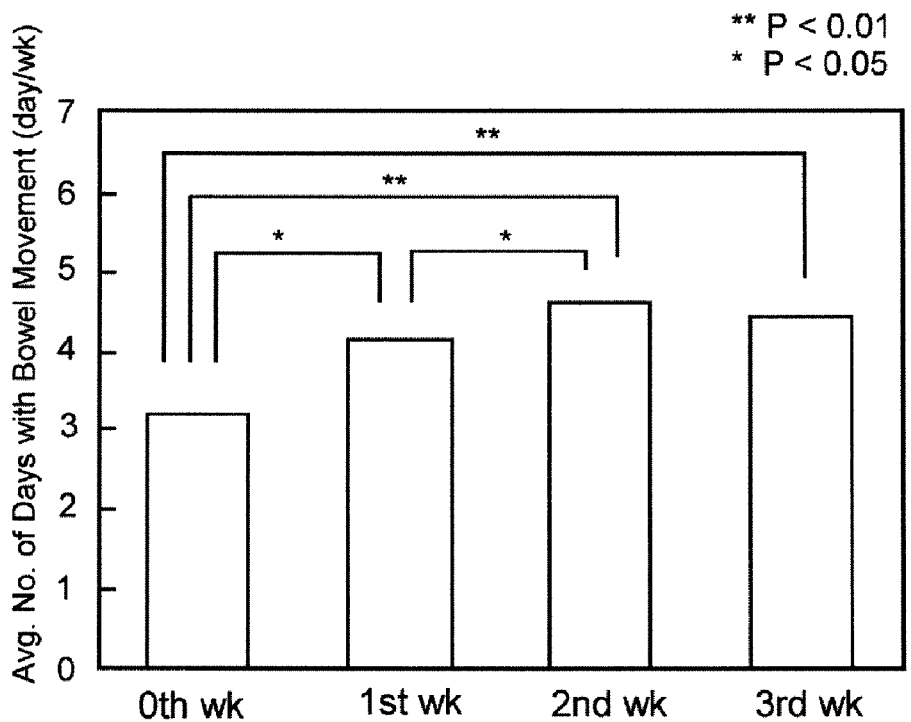
FIG. 24 is a graph showing the constipation relieving effect by a moist heating device according to the present invention.

As is apparent from the results shown in FIG. 24, applying the moist heating sheet to the abdomen for three weeks significantly increases the number of days with a bowel movement as compared with before the test, indicating an obvious effect on constipation relief.

Evaluation-5

Figure 8B:
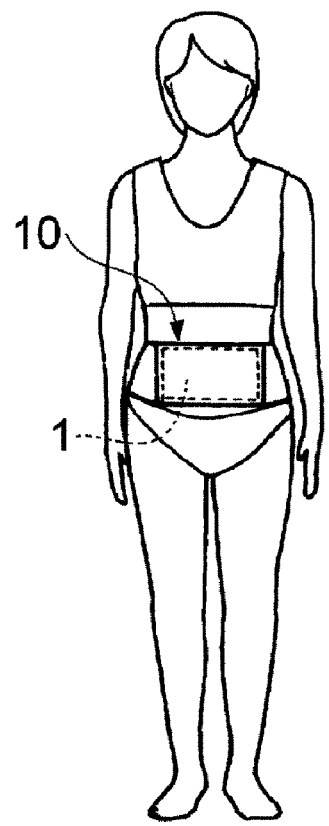

To confirm the effects of the moist heating sheet of the invention on regulation of the stomach, an activated state of the stomach motility was observed by means of an electrogastrograph. An electrogastrogram was recorded with Nipro EG (from Nipro Corp.) on four test subjects wearing the moist heating sheet or a dry heating sheet on their abdomen as illustrated in FIG. 8(b). The dry heating sheet had the same size and configuration as those of the moist heating sheet and was designed to produce substantially the same surface skin temperature in a bodily site where it was applied as that obtained by the moist heating sheet but not to generate steam. Each sheet was applied for 5 hours. The frequency of gastric contractions (2.4 to 3.6 cpm) was recorded before wearing, during wearing (at 2.5 hour application), and after detaching (immediately after 5 hour application) to obtain an average amplitude of the frequency. The results obtained are shown in FIG. 25.

Figure 25:
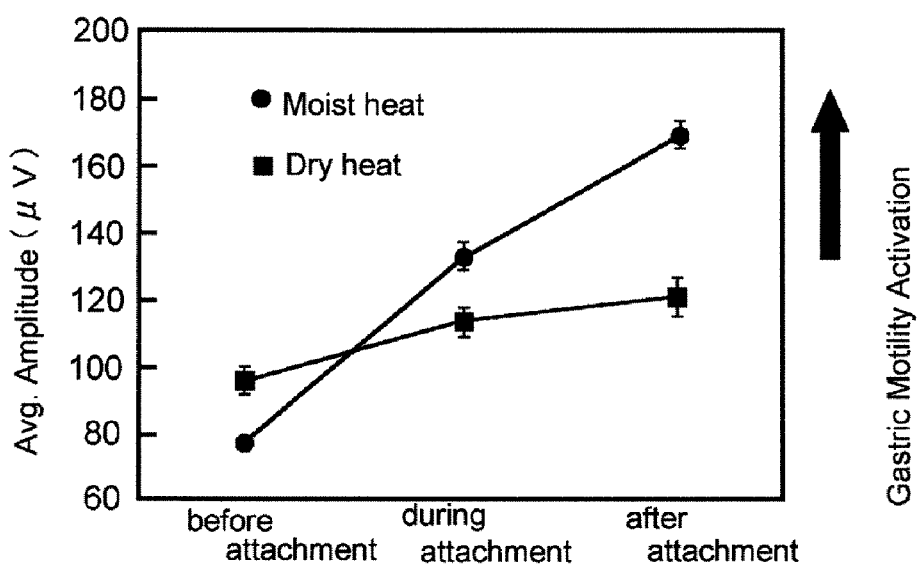
FIG. 25 is a graph showing the gastric motility activating effect by the moist heating device according to the present invention.

As is apparent from the graph shown in FIG. 25, the average amplitudes of the gastric contraction frequency markedly increases during and after the application of the moist heating sheet as compared with before the application. In contrast, applying the dry heating sheet does not bring about such a marked increase in average amplitude of the gastric contraction frequency. It is expected from these results that applying the moist heating sheet activates the gastric motility thereby regulating the stomach with, e.g., constipation relieving effects.

INDUSTRIAL APPLICABILITY

When applied to a human body, etc., the physiology enhancing device of the invention is capable of increasing not only the surface temperature of the application site but the deep body temperature. As a result, muscles relax, blood vessels dilate to increase the systemic blood flow, which leads to an increase in not only the body temperature at the application site but also a peripheral temperature (e.g., finger tip temperature). The physiology enhancing device is also effective in maintaining the peripheral temperature. A pain producing substance is removed with blood to relieve pain. Accordingly, the physiology enhancing device of the invention produces positive effects, such as blood circulation promotion, removal of tiredness from muscles, reduction of muscle stiffness or soreness, easing of oversensitivity to cold, and nerve pain relief. Application to the lower back is effective in relieving or eliminating lower back pain, and application to the abdomen is effective in relieving or eliminating abdominal pain. Application to the lower back and/or the abdomen also brings about improvement of visceral functions such as gastrointestinal functions and recovery from physical fatigue. An effect of easing menstrual cramps is also exhibited.

When applied to a human body, the moist heating device of the invention suppresses the sympathetic activity to make the parasympathetic nervous system dominant, resulting in giving a wearer a gentle feeling of relaxation as well as a feeling of warmth. The moist heating device of the invention alleviates or eliminates various pains such as a lower back pain or an abdominal pain and brings about improvements on various human physiological functions, including improvement of visceral functions such as gastrointestinal functions, easing or relief of constipation, and recovery from physical fatigue.

The invention claimed is:

1. A physiology enhancing device for improving physiological functions of a human body, comprising:
a heat generating element making use of chemical energy and a sheet interposed between the heat generating element and a body surface of a wearer, and which is designed to supply steam generated from the heat generating element while the device is applied to the body surface,
the physiology enhancing device having steam generating capability for 2 hours or longer and, when applied to the body surface, raising the temperature of the body surface to a temperature of from 38° C. to lower than 42° C. within one hour from the application.

2. The physiology enhancing device according to claim 1, wherein
the sheet interposed between the heat generating element and the body surface includes a moisture permeable film and a nonwoven fabric, and
the sheet has a function of regulating air feed to the heat generating element and a function of transferring the heat of the physiology enhancing device to the body surface and has a total thickness of 0.05 to 1.5 mm.

3. The physiology enhancing device according to claim 1 or 2, wherein the heat generating element is held in a holder, and the sheet interposed between the heat generating element and the body surface constitutes a part of the holder, the sheet having air permeability and moisture permeability, and the physiology enhancing device being configured such that heat generation proceeds from a peripheral portion to a central portion thereof.

4. The physiology enhancing device according to claim 3, wherein the holder comprises a sheet forming the outer facing side thereof and having a smaller value of water vapor transmission rate or a greater value of air permeance than the sheet interposed between the heat generating element of the physiology enhancing device and the body surface.

5. A physiology enhancing device for improving physiological functions of a human body, comprising:
a heat generating element making use of chemical energy and a sheet interposed between the heat generating element and a body surface of a wearer, and which is designed to supply steam generated from the heat generating element while the device is applied to the body surface,
the physiology enhancing device having steam supplying capability in a measuring environment of 20° C. and 40% RH such that the water content of the horny layer of a skin site to which the device is applied reaches 0.25 g/cm$^3$ or more after 0.5 hours from the start of application and that the water content of that level is maintained for 5 hours or longer from the start of application.

6. The physiology enhancing device according to claim 5, further having steam supplying capability in a measuring environment of 20° C. and 40% RH such that the humidity between the device and the skin site becomes 50% RH or higher after 0.5 hours from the start of application, that the humidity of that level is maintained for 5 hours or longer from the start of application, that the water content of the horny layer of the skin site reaches 0.25 to 0.39 g/cm$^3$ after 0.5 hours from the start of application, and that the water content of that level is maintained for 5 hours or longer from the start of application.

7. The physiology enhancing device according to claim 5 or 6, further having steam supplying capability such that the surface temperature of the skin site where the device is applied reaches a temperature from 38° C. to lower than 42° C. within one our from the start of application.

8. The physiology enhancing device according to claim 5, wherein
the sheet interposed between the heat generating element and the body surface includes a moisture permeable film and a nonwoven fabric, and
the sheet has a function of regulating air feed to the heat generating element and a function of transferring the heat generated from the device to the body surface and has a total thickness of 0.05 to 1.5 mm.

9. A moist heating device, comprising:
a heat generating element making use of chemical energy and a sheet interposed between the heat generating element and a body surface of a wearer, and which is designed to supply steam generated from the heat generating element while the device is applied to the body surface,
the sheet having at least an air permeable portion having a water vapor transmission rate of 150 to 2000 g/m$^2$·24 hr according to JIS Z0208 at 40° C. and 90% RH,
the heat generating element having steam generating capability such that the amount of steam released per unit time reaches the maximum in 0.5 to 25 minutes from the start of heat generation, and
the sheet interposed between the heat generating element and the body surface having a function of regulating air feed to the heat generating element and a function of transferring the heat of the moist heating device to the body surface and having a total thickness of 0.05 to 1.5 mm.

10. The moist heating device according to claim 9, wherein the heat generating element has steam generating capability such that a cumulative amount of steam released in 30 minutes from the start of heat generation is 0.1 to 0.5 g per gram of the heat generating element.

11. The moist heating device according to claim 10, wherein the heat generating element generates heat by making use of oxidation reaction of an oxidizable metal, the heat generating element is held in a holder having the air permeable portion, and the heat generating element contains the oxidizable metal, a water retaining agent, water, an electrolyte, and a reaction accelerator at a water retaining agent to water weight ratio of 0.26 to 0.60.

12. The moist heating device according to claim 11, wherein a weight ratio of the oxidizable metal to the reaction accelerator is 2 to 25.

13. The moist heating device according to claim 12, wherein the heat generating element comprises a sheet formed by a papermaking technique.

14. The moist heating device according to claim 12, wherein the heat generating element comprises powder.

15. The moist heating device according to claim 9, which is in a package labeled to an effect that the device is for relaxing a wearer's body.

16. A physiology enhancing device for improving physiological functions of a human body, comprising:
a heat generating element making use of chemical energy and a sheet interposed between the heat generating element and a body surface of a wearer, and which is designed to supply steam generated from the heat generating element while the device is applied to the body surface,
the physiology enhancing device having steam generating capability for 2 hours or longer and, when applied to the body surface, raising the temperature of the body surface to a temperature of from 38° C. to lower than 42° C. within one hour from the application,
the physiology enhancing device having a holder for holding the heat generating element,
the holder having a first air permeable layer and a second air permeable layer as the sheet,
the first air permeable layer being located farther from the wearer's skin while worn and having a first moisture permeable sheet,
the second air permeable layer being located closer to the wearer's skin while worn and having a second moisture permeable sheet, and
the water vapor transmission rate of the first air permeable layer (taken as A (m$^2$·24 hr)) and that of the second air permeable layer (taken as B (m$^2$·24 hr)) satisfying the following equations (1) to (3):

$$A+(B/3)=200\sim500 \text{ g}/(\text{m}^2\cdot24 \text{ hr}), \quad (1)$$

$$A+B=200\sim700 \text{ g}/(\text{m}^2\cdot24 \text{ hr}), \quad (2)$$

and $$B=100\sim450 \text{ g}/(\text{m}^2\cdot24 \text{ hr}) \quad (3).$$

17. A physiology enhancing device for improving physiological functions of a human body, comprising:
a heat generating element making use of chemical energy and a sheet interposed between the heat generating element and a body surface of a wearer, and which is designed to supply steam generated from the heat generating element while the device is applied to the body surface, the physiology enhancing device having steam supplying capability in a measuring environment of 20° C. and 40% RH such that the water content of the horny layer of a skin site to which the device is applied reaches 0.25 g/cm³ or more after 0.5 hours from the start of application and that the water content of that level is maintained for 5 hours or longer from the start of application, the physiology enhancing device having a holder for holding the heat generating element, the holder having a first air permeable layer and a second air permeable layer as the sheet, the first air permeable layer being located farther from the wearer's skin while worn and having a first moisture permeable sheet, the second air permeable layer being located closer to the wearer's skin while worn and having a second moisture permeable sheet, and the water vapor transmission rate of the first air permeable layer (taken as A (m²·24 hr)) and that of the second air permeable layer (taken as B (m²·24 hr)) satisfying the following equations (1) to (3):

$$A+(B/3)=200\sim500 \text{ g}/(\text{m}^2\cdot24 \text{ hr}), \quad (1)$$

$$A+B=200\sim700 \text{ g}/(\text{m}^2\cdot24 \text{ hr}), \quad (2)$$

and $$B=100\sim450 \text{ g}/(\text{m}^2\cdot24 \text{ hr}) \quad (3).$$

18. A moist heating device, comprising:

a heat generating element making use of chemical energy and a sheet interposed between the heat generating element and a body surface of a wearer, and which is designed to supply steam generated from the heat generating element while the device is applied to the body surface, the sheet having at least an air permeable portion having a water vapor transmission rate of 150 to 2000 g/m²·24 hr, the water vapor transmission rate being measured in accordance with JIS Z0208 at 40° C. and 90% RH, the heat generating element having steam generating capability such that the amount of steam released per unit time reaches the maximum in 0.5 to 25 minutes from the start of heat generation, and the sheet interposed between the heat generating element and the body surface having a function of regulating air feed to the heat generating element and a function of transferring the heat of the moist heating device to the body surface and having a total thickness of 0.05 to 1.5 mm, the physiology enhancing device having a holder for holding the heat generating element, the holder having a first air permeable layer and a second air permeable layer as the sheet, the first air permeable layer being located farther from the wearer's skin while worn and having a first moisture permeable sheet, the second air permeable layer being located closer to the wearer's skin while worn and having a second moisture permeable sheet, and the water vapor transmission rate of the first air permeable layer (taken as A (m²·24 hr)) and that of the second air permeable layer (taken as B (m²·24 hr)) satisfying the following equations (1) to (3):

$$A+(B/3)=200\sim500 \text{ g}/(\text{m}^2\cdot24 \text{ hr}), \quad (1)$$

$$A+B=200\sim700 \text{ g}/(\text{m}^2\cdot24 \text{ hr}), \quad (2)$$

and $$B=100\sim450 \text{ g}/(\text{m}^2\cdot24 \text{ hr}) \quad (3).$$

19. A method for alleviating oversensitivity to cold or nerve pain, comprising:

a step of applying to a human body a physiology enhancing device for improving physiological functions of a human body, the physiology enhancing device comprising a heat generating element making use of chemical energy and a sheet interposed between the heat generating element and a body surface of a wearer, and which is designed to supply steam generated from the heat generating element while the device is applied to the body surface, and the physiology enhancing device having steam generating capability for 2 hours or longer and, when applied to the body surface, raising the temperature of the body surface to a temperature of from 38° C. to lower than 42° C. within one hour from the application.

20. A method for alleviating lower back pain, comprising:

a step of applying to the lower back a physiology enhancing device for improving physiological functions of a human body, the physiology enhancing device comprising a heat generating element making use of chemical energy and a sheet interposed between the heat generating element and a body surface of a wearer, and which is designed to supply steam generated from the heat generating element while the device is applied to the body surface, and the physiology enhancing device having steam generating capability for 2 hours or longer and, when applied to the body surface, raising the temperature of the body surface to a temperature of from 38° C. to lower than 42° C. within one hour from the application.

21. A method for alleviating abdominal pain or constipation, comprising:

a step of applying to the abdomen a physiology enhancing device for improving physiological functions of a human body, the physiology enhancing device comprising a heat generating element making use of chemical energy and a sheet interposed between the heat generating element and a body surface of a wearer, and which is designed to supply steam generated from the heat generating element while the device is applied to the body surface, and the physiology enhancing device having steam generating capability for 2 hours or longer and, when applied to the body surface, raising the temperature of the body surface to a temperature of from 38° C. to lower than 42° C. within one hour from the application.

22. A method for recovering a wearer's body from fatigue, comprising:

a step of applying to the abdomen and/or the lower back a physiology enhancing device for improving physiological functions of a human body, the physiology enhancing device comprising a heat generating element making use of chemical energy and a sheet interposed between the heat generating element and a body surface of a wearer, and which is designed to supply steam generated from the heat generating element while the device is applied to the body surface, and the physiology enhancing device having steam generating capability for 2 hours or longer and, when applied to the body surface, raising the temperature of the body surface to a temperature of from 38° C. to lower than 42° C. within one hour from the application.

23. A method for relaxing a wearer's body, comprising:
a step of applying to a human body a physiology enhancing device for improving physiological functions of a human body,
the physiology enhancing device comprising a heat generating element making use of chemical energy and a sheet interposed between the heat generating element and a body surface of a wearer, and which is designed to supply steam generated from the heat generating element while the device is applied to the body surface, and
the physiology enhancing device having steam generating capability for 2 hours or longer and, when applied to the body surface, raising the temperature of the body surface to a temperature of from 38° C. to lower than 42° C. within one hour from the application.

24. A physiology enhancing device for improving physiological functions of a human body, comprising:
a heat generating element making use of heat of oxidation generated by oxidation reaction of an oxidizable metal as chemical energy and a sheet interposed between the heat generating element and a body surface of a wearer, and which is designed to supply steam generated from the heat generating element while the device is applied to the body surface,
the physiology enhancing device having steam generating capability for 2 hours or longer and, when applied to the body surface, raising the temperature of the body surface to a temperature of from 38° C. to lower than 42° C. within one hour from the application,
the sheet interposed between the heat generating element of the physiology enhancing device and a body surface of a wearer having a function of controlling air feed to the heat generating element of the physiology enhancing device and a function of transferring the heat generated of the physiology enhancing device to the body surface, the sheet having a total thickness of 0.05 to 1.5 mm,
the heat generating element having a water content of 30 to 70% and being contained in a holder, and the sheet interposed between the heat generating element of the physiology enhancing device and a body surface of a wearer constituting a part of the holder and having air permeability and moisture permeability,
a sheet which forms the outer facing side of the holder having smaller value of the water vapor transmission rate or a greater value of air permeance than the sheet interposed between the heat generating element of the physiology enhancing device and a body surface,
the sheet interposed between the heat generating element of the physiology enhancing device and a body surface of a wearer being a sheet of a single layer structure formed of a moisture permeable film, being a sheet of a dual layer structure formed of the moisture permeable film and nonwoven fabric, being a sheet of a multilayer structure having three or more sheets formed of a combination of a moisture permeable film and two or more of nonwoven fabrics of the same or different kinds and being brought in direct contact with a body surface, or being a combination of the single layer structure, the dual layer structure or the multilayer structure and a water vapor permeable material in which the single structure, the dual structure or the multilayer structure is brought into contact with a body surface via the water vapor permeable material, and
the physiology enhancing device being made to generate the heat to proceed from the peripheral of the physiology enhancing device toward the central portions of the physiology enhancing device.

* * * * *